United States Patent [19]

Yuasa et al.

[11] Patent Number: 4,764,497
[45] Date of Patent: Aug. 16, 1988

[54] AMORPHOUS, SPHERICAL INORGANIC COMPOUND AND PROCESS FOR PREPARATION THEREOF

[75] Inventors: Shigeki Yuasa; Minahiro Okabayashi, both of Fujisawa; Hideki Ohno; Katsumi Suzuki, both of Sagamihara; Koshi Kusumoto, Yokohama, all of Japan

[73] Assignee: Tokuyama Soda Kabushiki Kaisha, Yamaguchi, Japan

[21] Appl. No.: 804,181

[22] Filed: Dec. 3, 1985

Related U.S. Application Data

[62] Division of Ser. No. 452,735, Dec. 23, 1982, Pat. No. 4,567,030.

[30] Foreign Application Priority Data

Dec. 23, 1981 [JP] Japan ................. 56-206862

[51] Int. Cl.$^4$ ........................................... C01B 33/20
[52] U.S. Cl. ................................. 502/235; 502/236; 502/242
[58] Field of Search ................. 502/235, 236, 242

[56] References Cited

U.S. PATENT DOCUMENTS

| 3,137,658 | 6/1964 | Drake et al. | 502/236 |
|---|---|---|---|
| 3,709,883 | 1/1973 | Thomas | 252/402 |
| 3,973,972 | 8/1976 | Muller | 501/64 |
| 4,018,816 | 4/1977 | Onoda et al. | 502/236 |
| 4,176,089 | 11/1979 | Cull | 502/236 |
| 4,424,320 | 1/1984 | McDaniel | 502/236 |
| 4,476,243 | 10/1984 | Dombro | 502/236 |

FOREIGN PATENT DOCUMENTS

| 1468302 | 9/1963 | Fed. Rep. of Germany | 502/236 |
|---|---|---|---|
| 19520-75 | 9/1975 | Japan | 502/236 |
| 3104-80 | 5/1980 | Japan | 502/236 |

OTHER PUBLICATIONS

W. Strober et al., "Controlled Growth of Monodisperse Silica Spheres in the Micron Size Range," J. of Colloid & Interface Science, 26, 62-69 (1968).

Masayuki Nogami et al., "On the Properties of Non-Crystalline Films Containing TiO$_2$ and ZrO$_2$ Prepared from Metal Alkoxides," 85 (9) 44.

Sumio Sakka et al., "Glasses from Metal Alcoholates," J. of Non-Crystalline Solids, 42, 403-422 (1980).

Akio Makishima et al., "Alkaline Durabilities and Structures of Amorphous Aluminosilicates Containing ZrO$_2$ Prepared by the Chemical Polymerization of Metal Alkoxides," J. of Non-Crystalline Solids, 43, 545-552 (1980).

Yamane et al., "Low Temperature Synthesis of Non-Crystalline Solids of the System SrO-SiO$_2$," J. of Non-Crystalline Solids, 44, 181-190 (1981).

Kamiya et al., "Structure and Properties of TiO$_2$-SiO$_2$ Glasses Prepared from Metal Alkoxides," Nippon Kagaku Kaisha, 10, 1571-1576 (1981).

Primary Examiner—John Doll
Assistant Examiner—Wayne A. Langel
Attorney, Agent, or Firm—Sherman and Shalloway

[57] ABSTRACT

Disclosed is an amorphous, spherical inorganic compound having a particle size of 0.1 to 1.0 μm, which comprises as main constituents (1) an oxide of at least one metal selected from the group consisting of metals of the Groups I, II, III and IV of the Periodic Table, said metal oxide being capable of combining with silicon dioxide, and (2) silica.

This amorphous, spherical inorganic compound is prepared by a process comprising adding a mixed solution containing a hydrolyzable organic silicon compound and a hydrolyzable organic compound of at least one metal (M) selected from the group consisting of metals of the Groups I, II, III and IV of the Periodic Table to an alkaline solvent capable of dissolving said organic silicon compound and said organic metal compound therein but substantially incapable of dissolving a reaction product of both the organic silicon compound and the organic metal compound therein, effecting the hydrolysis to precipitate the reaction product and, if necessary, calcining the reaction product.

21 Claims, 3 Drawing Sheets x 20,000 x 20,000 x 15,000

AMORPHOUS, SPHERICAL INORGANIC COMPOUND AND PROCESS FOR PREPARATION THEREOF

This is a division of application Ser. No. 452,735, filed Dec. 23, 1982, now U.S. Pat. No. 4,567,030.

BACKGROUND OF THE INVENTION (1) Field of the Invention

The present invention relates to an amorphous, spherical inorganic compound comprising as main constituents (1) an oxide of at least one metal selected from the group consisting of metals of the Groups I, II, III and IV of the Periodic Table and (2) silica, and a process for the preparation thereof.

Incidentally, by the term "amorphous compound" is meant a compound having a crystallinity lower than 50%.

(2) Description of the Prior Art

Powdery inorganic compounds comprising as main constituents a specific metal oxide and silica have been known. It has also been known that these inorganic compounds can be prepared according to a method comprising mixing silica with a metal oxide, melting the mixture at a high temperature higher than the melting point of the mixture to obtain a vitreous substance and pulverizing the vitreous substance. The powdery product obtained according to this known method, however, has an indeterminate shape and a very broad particle size distribution, and therefore, it can be applied only to much limited uses. As another method, there is known a method comprising mixing a silicon alkoxide with a titanium alkoxide, hydrolyzing these alkoxides to obtain a gel and sintering the gel product to obtain an inorganic compound composed of silica and titania [see Nippon Kagaku Kaishi, 10, 1571 (1981)]. This method is advantageous over the above-mentioned method in that the gel can be formed into various shapes, for example, a plate and a fiber. Even if this method is adopted, however, it is impossible to obtain an amorphous inorganic compound having a spherical shape, a small particle size, for example, from 0.1 to 1.0 $\mu$m and especially a narrow particle size distribution. In other words, it has been an important technical problem how to obtain an amorphous, spherical inorganic compound uniform in the particle size, which comprises as main constituents silica and a metal oxide.

SUMMARY OF THE INVENTION

It is therefore a primary object of the present invention to provide an amorphous, spherical inorganic compound having a particle size of 0.1 to 1.0 $\mu$m, which comprises as main constituents (1) an oxide of at least one metal selected from the group consisting of metals of the Groups I, II, III and IV of the Periodic Table and (2) silica, and a process for the preparation thereof.

Another object of the present invention is to provide a substantially non-agglomerating inorganic compound having a particle size of 0.1 to 1.0 $\mu$m and a very narrow particle size distribution, and a process for the preparation thereof.

Still another object of the present invention is to provide an amorphous, spherical inorganic compound having a particle size of 0.1 to 1.0 $\mu$m, which comprises as main constituents a specific metal oxide and silica and which provides a composite material excellent in not only the mechanical strength and surface hardness but also the transparency and surface smoothness when used as a reinforcer for the composite material.

We made researches with a view to solving the above-mentioned technical problem and we succeeded in preparing an amorphous, spherical inorganic compound having a particle size of 0.1 to 1.0 $\mu$m, which comprises as main constituents (1) an oxide of at least one metal selected from the group consisting of metals of the Groups I, II, III and IV of the Periodic Table and (2) silica. Thus, we have now completed the present invention.

More specifically, in accordance with one aspect of the present invention, there is provided an amorphous, spherical inorganic compound having a particle size of 0.1 to 1.0 $\mu$m, which comprises as main constituents (1) an oxide of at least one metal selected from the group consisting of metals of the Groups I, II, III and IV of the Periodic Table, said metal oxide being capable of combining with silicon dioxide, and (2) silica.

In accordance with another aspect of the present invention, there is provided a process for the preparation of amorphous inorganic compounds, which comprises adding a mixed-solution containing a hydrolyzable organic silicon compound and a hydrolyzable organic compound of at least one metal (M) selected from the group consisting of metals of the Groups I, II, III and IV of the Periodic Table to an alkaline solvent capable of dissolving said organic silicon compound and said organic compound therein but substantially incapable of dissolving a reaction product of both the organic silicon compound and the organic metal compound therein, effecting the hydrolysis to precipitate the reaction product and, if necessary, calcining the reaction product.

Other objects and features of the present invention will become apparent from the following detailed description.

DETAILED DESCRIPTION OF THE INVENTION

Figure 1:
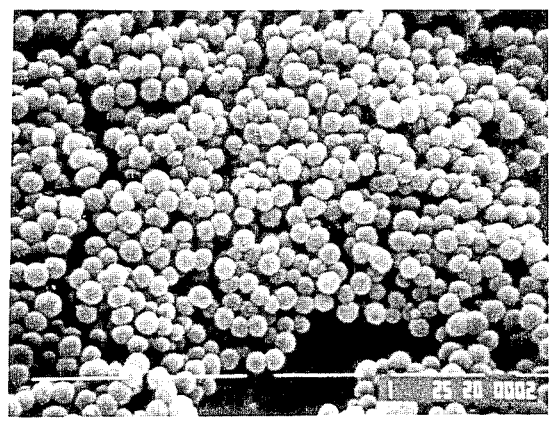
FIG. 1 is a scanning electron microscope photograph (20000 magnifications) of $SiO_2/TiO_2$ spherical particles obtained in Example 4.
Figure 2:
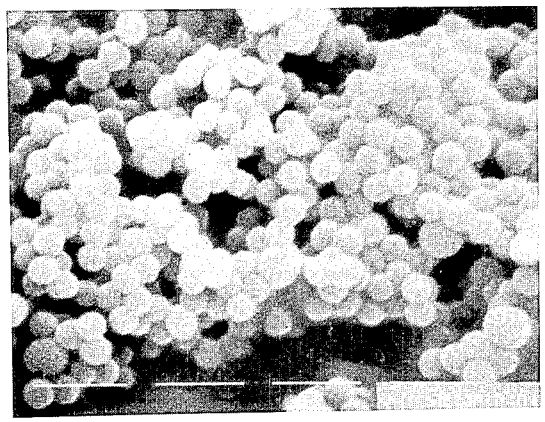
FIG. 2 is a scanning electron microscope photograph (20000 magnifications) of $SiO_2/TiO_2/Na_2O$ spherical particles obtained in Example 100.
Figure 3:
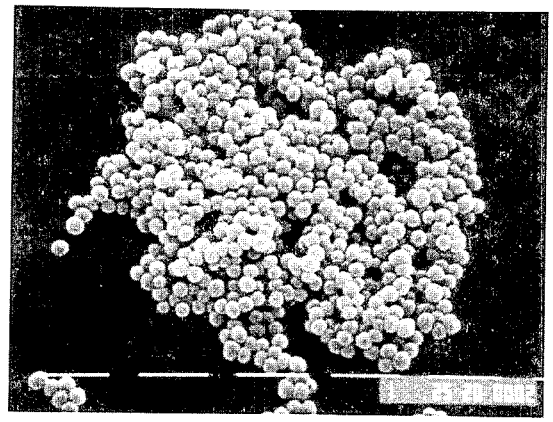
FIG. 3 is a scanning electron microscope photograph (15000 magnifications) of $SiO_2/SrO/ZrO_2$ sperical particles obtained in Example 95.

In the inorganic compound of the present invention, at least one metal oxide selected from the group consisting of oxides of metals of the Groups I, II, III and IV of the Periodic table, such as lithium oxide, potassium oxide, sodium oxide, magnesium oxide, calcium oxide, strontium oxide, barium oxide, aluminum oxide, boron oxide, yttrium oxide, titanium oxide, zirconium oxide, hafnium oxide, tin oxide and lead oxide, forms a solid solution with silica. In short, the inorganic compound of the present invention comprises silica and the above-mentioned metal oxide as the main constituents.

Incidentally, in the description given hereinafter, the metals of the Groups I, II, III and IV of the Periodic Table are abbreviated to $M^1$, $M^2$, $M^3$ and $M^4$, respectively, and the symbol "M" is used as a general symbol for these metals $M^1$ through $M^4$. Accordingly, $MO_{x/2}$ is used as a general symbol for oxides of metals $M^1$ through $M^4$, in which x indicates the valency of the metal M ion.

The content of the metal oxide $MO_{x/2}$ in the inorganic compound has great influences on the shape of the inorganic compound. Of course, these influences of the content of the metal oxide $MO_{x/2}$ on the shape of the inorganic compound are changed according to the kind of $MO_{x/2}$, the preparation process and the preparation conditions. However, in order to obtain a spherical inorganic compound, it is generally preferred that the content of $MO_{x/2}$ be controlled to a level of up to 20 mole %, and if the content of $MO_{x/2}$ is adjusted to 0.01 to 15 mole %, an inorganic compound having a shape of a substantially true sphere and a uniform particle size can be obtained. The content of $MO_{x/2}$ can be confirmed by the chemical analysis, and in case of certain $MO_{x/2}$, its content can be confirmed by the fluorescent X-ray analysis. Ordinarily, the content of $MO_{x/2}$ is not substantially different from the value calculated theoretically from the composition of the starting compounds. Accordingly, if the composition of the starting compounds is known, the content of $MO_{x/2}$ can be calculated from this composition.

In the inorganic compound of the present invention, the constituents, that is, silica and $MO_{x/2}$, are ordinarily present in the chemically bonded state and they cannot be separated from each other. The fact that both the constituents are chemically bonded to each other can be confirmed by measuring the infrared spectrum and refractive index of the inorganic compound.

The shape, particle size and particle size distribution of the inorganic compound of the present invention can be determined from a scanning or transmission electron microscope photograph. The particle size of the inorganic compound of the present invention is very small and in the range of, for example, from 0.1 to 1.0 μm, and the particle size distribution is very narrow. For example, the standard deviation value of the particle size can be controlled below 1.30.

From scanning electron microscope photographs of typical instances of the spherical inorganic compounds, shown in the accompanying drawings, it will readily be understood that the inorganic compound of the present invention is composed of uniform particles having a shape of a true sphere and having a non-agglomerating property.

The inorganic compound of the present invention comprising silica and $MO_{x/2}$ as the main constituents is divided into two types; one having a specific surface area of at least 100 $m^2/g$, ordinarily 100 to 200 $m^2/g$, and the other having a specific surface area smaller than 100 $m^2/g$, ordinarily 1 to 100 $m^2/g$, especially 1 to 50 $m^2/g$. An inorganic compound obtained by reacting and hydrolyzing starting compounds of both the constituents in an alkaline solvent as described in detail hereinafter has ordinarily a specific surface area of at least 100 $m^2/g$. If this inorganic compound is calcining at a temperature of at least 500° C., ordinarily 500° to 1300° C., the specific surface area of the inorganic compound is reduced below 100 $m^2/g$. In each of these inorganic compounds, however, the contents of the constituents are not substantially changed, and the shape of the particles is substantially spherical.

The inorganic compound of the present invention is substantially amorphous or is a mixture comprising the majority of an amorphous portion and the minority of a crystalline portion. This can be determined by analyzing the inorganic compound of the present invention by the X-ray diffractometry or the measurement of the refractive index.

The inorganic compound of the present invention has —OH groups bonded to the surface thereof. The amount of the —OH groups can be determined by the alkali neutralization method. The —OH group content is ordinarily 1.0 to 2.0 millimoles per gram in the inorganic compound having a larger specific surface area, that is, the inorganic compound before calcining, and the —OH group content is ordinarily 0.01 to 0.10 millimole per gram in the inorganic compound having a smaller specific surface area, that is, the inorganic compound after calcining.

The specific gravity and refractive index of the inorganic compound of the present invention cannot generally be defined, because they differ according to the kind and content of $MO_{x/2}$. In most cases, however, the specific gravity is in the range of 1.20 to 3.00 and the refractive index is in the range of 1.35 to 1.70.

As pointed out hereinbefore, the inorganic compound of the present invention is characterized in that the particle size is from 0.1 to 1.0 μm and the shape is spherical. The inorganic compound of the present invention is effectively used in the fields where this characteristic feature is utilized. For example, when the inorganic compound of the present invention is used as a filler for a dental material, the filling ratio can be increased, and therefore, the mechanical strength and surface hardness of the obtained dental composite material can be enhanced. Furthermore, the transparency and surface smoothness can be improved. Namely, practically valuable effects can be attained by incorporation of the inorganic compound of the present invention. Moreover, the inorganic compound of the present invention can preferably be used as a catalyst, a catalyst carrier, a sintering aid, a pigment, an inorganic ion exchanger and an adsorbent widely in various fields.

The inorganic compound of the present invention has various characteristic properties as described above and can be used in various fields. The process for the preparation of the inorganic compound of the present invention is not particularly critical, so far as the above-mentioned characteristic properties are given to the product. Typical instances of the preparation process will now be described.

(1) According to one embodiment of the preparation process of the present invention, a mixed solution containing a hydrolyzable organic silicon compound and a hydrolyzable organic compound of at least one metal (M) selected from the group consisting of metals of the Groups I, II, III and IV of the Periodic Table is added to an alkaline solvent capable of dissolving the organic silicon compound and the organic metal compound therein but substantially incapable of dissolving a reaction product of the organic silicon compound and the organic metal compound therein and the hydrolysis is effected to precipitate the reaction product.

Various organic silicon compounds can be mentioned as the hydrolyzable organic silicon compound. For example, as industrially easily available alkoxy-substituted silicon compounds, there can be mentioned silicon alkoxides represented by the general formula $Si(OR)_4$ and low condensates obtained by partial hydrolysis of these silicon alkoxides, and they can be used without any particular limitation. In the above general formula, R stands for an alkyl group, and ordinarily, lower alkyl groups such as methyl, ethyl, isopropyl and butyl groups are preferred as R. Commercially available products of these silicon akoxides and low condensates thereof can be used directly or after purification by distillation.

As the hydrolyzable organic metal compound as the other reactant, there are preferably used alkoxy-substituted organic metal compounds, such as metal alkoxides represented by the general formula $M_x(OR')_x$ in which R' stands for an alkyl group and x is an integer of $1 \leq x \leq 4$, and compounds of the above formula in which one alkoxide group (OR') in case of x=2 or one or two alkoxide groups (OR') in case of x=3 or 4 are substituted by carboxyl or β-dicarbonyl groups.

Preferred examples of the organic metal compound are as follows.

With respect to $M^1$, there can be mentioned organic sodium compounds such as $NaOCH_3$, $NaOC_2H_5$, $NaOC_3H_7$ and $CH_3COONa$, and corresponding organic Li and K compounds. With respect to $M^2$, there can be mentioned organic magnesium compounds such as $Mg(O-iso-C_3H_7)_2$, $Mg(O-n-C_4H_9)_2$, $Mg(O-iso-C_5H_{11})_2$, $Mg(OCH_3)_2$ and $Mg(OC_2H_5)_2$, and corresponding organic Ca, Sr and Ba compounds. With respect to $M^3$, there can be mentioned organic aluminum compounds such as $Al(O-iso-C_3H_7)_3$, $Al(O-n-C_4H_9)_3$, $Al(O-sec-C_4H_9)_3$ and $Al(O-n-C_4H_9)(O-iso-C_3H_7)_2$, and corresponding organic B, Ga, Sc, La, Y and In compounds. With respect to $M^4$, there can be mentioned organic titanium compounds such as $Ti(O-iso-C_3H_7)_4$, $Ti(O-n-C_4H_9)_4$, $Ti[O-CH_2CH(C_2H_5)C_4H_9]_4$, $Ti(O-C_{17}H_{35})_4$, $Ti(O-iso-C_3H_7)_2[CO(CH_3)CHCOCH_3]_2$, $Ti(O-n-C_4H_9)_2[OC_2H_4N(C_2H_4OH)_2]_2$, $Ti(OH)_2[OCH(CH_3)COOH]_2$, $Ti[OCH_2CH(C_2H_5)CH(OH)C_3H_7]_4$ and $Ti(O-n-C_4H_9)_2(OCOC_{17}H_{35})_2$, and corresponding organic Zr, Ge, Hf, Sn and Pb compounds.

In the present invention, the silicon alkoxide or its low condensate is preliminarily mixed with the organic metal compound to form a mixed solution. Any of solvents capable of dissolving the foregoing starting compounds therein can be used without any particular limitation. However, from the viewpoints of the reactivity described hereinafter, the operation adaptability and the availability, it is preferred that an alcoholic solvent such as methanol, ethanol, isopropanol, butanol, ethylene glycol or propylene glycol be used. Furthermore, an ether type solvent such as dioxane or diethyl ether or an ester type solvent such as ethyl acetate may be used in the form of a mixture with an alcoholic solvent such as described above. There is ordinarily adopted a method in which the starting compounds are independently dissolved in the solvent and the resulting solutions are mixed. There can also be adopted a method in which one reactant is dissolved in the solvent and the other reactant is incorporated and dissolved in the formed solution. It is ordinarily preferred that the concentration of the mixed solution of the starting compounds be low. However, if the concentration is too low, the amount used of the solvent is drastically increased. If the concentration is too high, control of the reaction becomes difficult and handling of the mixed solution becomes troublesome. Accordingly, the concentration is appropriately determined while taking the foregoing into consideration. It is ordinarily preferred that the concentration of the mixed solution be up to 50% by weight, especially 5 to 50% by weight.

In order to impart a spherical shape to the inorganic compound of the present invention, it is preferred to control the mixing ratio of silicon (Si) and the above-mentioned metal (M) in the mixed solution of the starting compounds and, if necessary, the amount of water added to the mixed solution. Water is contained in the solvent for the mixed solution of the starting compounds or water is positively added so as to hydrolyze the starting organic silicon compound. If the amount of water is too much, it is ordinarily difficult to impart a spherical shape to the inorganic compound and the inorganic compound tends to have an indeterminate shape. Accordingly, in order to obtain a spherical inorganic compound, it is preferred that the amount of water in the mixed solution be smaller. Ordinarily, good results can be obtained if the amount of water is selected so that the requirements of $H_2O/M \geq 1.0$, preferably $H_2O/M \geq 2.0$, and $H_2O/Si \leq 4$, preferably $H_2O/Si \leq 1.0$, are satisfied.

When the organic metal compound used in the present invention is an organic compound of a metal of the Group I, II or III of the Periodic Table, incorporation of water is not particularly necessary, but when the organic metal compound is an organic compound of a metal of the Group IV of the Periodic Table, it is preferred that the mixed solution containing water in the above-mentioned amount be used. Incidentally, if the metal of the Group IV of the Periodic Table is zirconium, incorporation of water is not particularly necessary.

It also is preferred that the mixing ratio of Si and M added to the mixed solution be controlled. Namely, it is preferred that the amounts of the starting compounds be selected so that the requirement of $M/(Si+M) \leq 0.3$, especially $M/(Si+M) \leq 0.2$, is satisfied.

It has not completely been elucidated what actions the above conditions impose on formation of the inorganic compound. However, it is construed that if water is present in the mixed solution, a low condensate of the organic silicon compound is formed as an intermediate during the process of formation of the inorganic compound. This can be confirmed by the following fact. For example, when water is added to tetraethyl silicate [Si(OEt)$_4$] and hydrolysis is carried out, by analyzing means such as gas chromatography, it can be confirmed that the following intermediates having a silanol group are present:

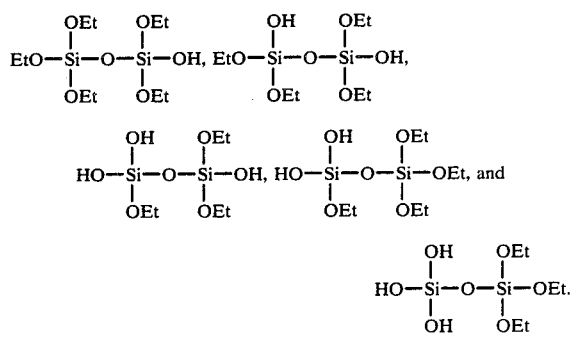

These intermediates are rich in the reactivity and they react mutually or with other ethyl silicates, and they are extinguished by the alcohol-removing reaction while forming high condensates. In the case where amounts formed of these intermediates are appropriate, the inorganic compound, which is a final reaction product, comes to have a spherical shape. When a distillation product of commercially available tetraethyl silicate is used as the starting compound, the intended intermediates can be obtained after passage of 2 to 3 hours at 25° C. or several minutes to about 10 minutes at 60° C. from the point of addition of a predetermined amount of water. However, in case of a starting compound which is hardly hydrolyzable, the hydrolysis can be promoted by addition of a hydrolysis promoter, for example, a mineral acid such as hydrochloric acid or nitric acid or an ion exchange resin. In the case where the hydrolysis promoter is added, since the hydrolysis rate is changed according to the amount added of the hydrolysis promoter, it is recommendable to preliminarily determine conditions for hydrolyzing the starting compound to an appropriate degree. From the foregoing description, it will be understood that whether or not the resulting inorganic compound will be able to have a spherical shape is significantly influenced by the amount of water in the mixed solution, that is, the amount of water for hydrolyzing tetraethyl silicate.

In the case where water is not present in the mixed solution, it is presumed that a certain intermediate may be formed by the reaction between the organic silicon compound and the organic metal compound, though the ground for this presumption is not definite.

The ratio of M and Si present in the starting mixed solution has influences on the refractive index of the obtained inorganic compound. Accordingly, the refractive index can be adjusted by appropriately controlling the above ratio.

Even if the organic silicon compound and the organic metal compound are independently added to an alkaline solvent described hereinafter and are reacted without mixing the organic silicon compound with the organic metal compound, the intended inorganic compound, especially one having a spherical shape, cannot be obtained. In preparing the inorganic compound of the present invention, therefore, it is indispensable that a mixed solution of both the starting compounds should be prepared in advance. The conditions for preparing the mixed solution is not particularly critical, but in order to uniformly disperse both the reactants and react them, it is ordinarily preferred to stir the solution or allow the solution to stand still at 0° to 100° C. for several minutes to several hours.

The so-prepared mixed solution of both the starting compounds is added to an alkaline solvent capable of dissolving both the starting compound therein but substantially incapable of dissolving the inorganic compound as the reaction product therein and the resulting mixture is stirred to precipitate the inorganic compound comprising as main constituents (1) an oxide of at least one metal selected from the group consisting of metals of the Groups I, II, III and IV of the Periodic Table and (2) silica. Known organic solvents can be used without any limitation, so far as they are capable of dissolving both the starting compounds therein but substantially incapable of dissolving the formed inorganic compound therein. A solvent preferably used is an aqueous solution comprising water and an alcoholic solvent as described above as the solvent for the organic silicon compound and the organic metal compound or a mixture of this alcoholic solvent with an organic solvent such as an ether type solvent or ester type solvent. As pointed out hereinbefore, it is indispensable that this aqueous solvent should be alkaline. A known compound may be used for rendering the aqueous solvent alkaline, but ordinarily, ammonia is most preferred.

The particle size of the inorganic compound of the present invention is influenced by such factors as the kind of the organic solvent, the amount of water and the alkali concentration. Accordingly, it is preferred that these conditions are preliminarily set. It is ordinarily preferred that the alkali concentration be selected within the range of 1.0 to 10 mole/l, and there is observed a tendency that the higher is the alkali concentration, the larger is the particle size of the obtained inorganic compound. The amount of water is important for promoting the hydrolysis and forming the intended inorganic compound, and the amount of water is ordinarily selected within the range of 0.5 to 50 mole/m. As the concentration of water is higher, the particle size of the inorganic compound tends to increase. Another factor having influences on the particle size of the inorganic compound is the kind of the organic solvent, and as the number of carbon atoms of the organic solvent is larger, the particle size of the inorganic compound ordinarily tends to increase.

The method for adding the mixed solution of the starting compounds to the alkaline solvent is not particularly critical, but it is ordinarily preferred that the mixed solution be added little by little over a period of a long time. Generally, good results can be obtained when the mixed solution is added over a period of several minutes to several hours. The reaction temperature is changed according to various reaction conditions and it is difficult to generally define the reaction temperature, but it is ordinarily preferred that the reaction be carried out at 0° to 40° C., especially about 10° to about 30° C., under atmospheric pressure. Although the reaction may be carried out under a reduced pressure or an elevated pressure, it is preferred that the reaction be carried out under atmospheric pressure, because the reaction is sufficiently advanced under atmospheric pressure.

The reaction product precipitated by the above reaction procedures is separated and then dried. The so-obtained inorganic compound comprises silica and $MO_{x/2}$ as the main constituents as pointed out hereinbefore, and it has a specific surface area of at least 100 $m^2/g$. If the above-mentioned various conditions are selected, there can be obtained an inorganic compound having a particle size of 0.1 to 1.0 μm and such an excellent particle size distribution that the standard deviation value is smaller than 1.30.

(2) Seeds composed of silicon dioxide are incorporated in the alkaline solvent in advance as core for precipitation of the inorganic compound in the above-mentioned method (1), and the reaction is then carried out in the same manner as in the method (1) to obtain the intended inorganic compound.

Particles composed of silica, that is, silicon dioxide, may be used as the seeds without any limitation. The method for making such seeds present is not particularly critical. For example, there may preferably be adopted a method in which particles already separated are dispersed in the alkaline solvent or a method in which particles are formed in the alkaline solvent and they are used as seeds without separation. The latter method will now be described in detail. A silicon alkoxide or its low condensate is hydrolyzed in advance to form seeds and the reaction is carried out in the presence of the so-formed seeds in the same manner as in the method (1) to obtain the intended inorganic compound. The silicon alkoxide or its low condensate is hydrolyzed in a solvent capable of dissolving the silicon alkoxide therein but incapable of dissolving the formed seeds therein. The seeds act as core for the finally formed inorganic compound. The seeds need not particularly have a size that can be confirmed with the naked eye in the state dispersed in the solvent, but they may be in the form of fine particles that cannot be confirmed with the naked eye. The method for forming such seeds from the silicon alkoxide or its low condensate is not particularly critical, but any of known hydrolysis methods can be adopted. For example, as described hereinbefore with respect to the method (1), there may be adopted a method in which a specific amount of water is made present in an alkaline solvent such as mentioned above with respect to the method (1) and the silicon alkoxide or its low condensate is added. Although the silicon alkoxide or its low condensate may directly be added, it is preferred that as described hereinbefore with respect to the method (1), the silicon alkoxide or its low condensate be dissolved in a solvent capable of dissolving the silicon alkoxide or its low condensate therein and the silicon alkoxide or its low condensate be added in the form of a solution having a concentration adjusted to 1 to 50% by weight.

After formation of the seeds, the inorganic compound is precipitated and then separated and dried in the same manner as in the above-mentioned method (1). Since the so-obtained inorganic compound comprises as main constituents silica and $MO_{x/2}$ formed on silica as the core, the particle size distribution of the inorganic compound is especially excellent. The specific surface area of the obtained inorganic compound is at least 100 $m^2/g$ and the particle size thereof is from about 0.1 to about 1.0 $\mu m$.

(3) A mixed solution containing a hydrolyzable organic silicon compound and a hydrolyzable organic compound of at least one metal selected from the group consisting of metals of the Groups I, II, III and IV of the Periodic Table is added to an alkaline solvent capable of dissolving the organic silicon compound and the organic metal compound but incapable of dissolving a reaction product of the organic silicon compound and the organic metal compound to effect the hydrolysis and precipitate the reaction product, and a hydrolyzable organic silicon compound is added to the reaction mixture to effect the hydrolysis thereof.

In the method (3), the operations for precipitating the inorganic compound comprising silica and $MO_{x/2}$ as the main constituents are the same as in the method (1), but in the method (3), after formation of the precipitate of the inorganic compound, an organic silicon compound is added and reacted. Organic silicon compounds to be used as the starting compound may be used as the organic silicon compound to be finally reacted without any particular limitation. For example, an alkoxy-substituted silicon compound or its low condensate is especially preferably used. The method for reacting the organic silicon compound with the precipitate is not particularly critical, and any of known methods may be adopted. For example, there may be adopted a method in which a solution of the organic silicon compound is added to the alkaline solvent containing the precipitate or a slurry formed by dispersing the once separated precipitate in a solvent incapable of dissolving the precipitate. The same solvent as used for dissolving the starting organic silicon compound is preferably used as the solvent for dissolving the organic silicon compound to be finally added. Since the organic silicon compound should be hydrolyzed so as to react it with the precipitate, it is preferred that water be made present in the above reaction solvent according to need. The amount of water is the same as described hereinbefore with respect to the condition for precipitating the reaction product comprising silica and $MO_{x/2}$ as the main constituents in the method (1). Ordinarily, it is preferred that when the solvent containing the organic silicon compound dissolved therein is added to the solution containing the precipitate of the above reaction product to effect reaction, the concentration of the organic silicon compound be low, for example, up to 50% by weight, especially 1 to 30% by weight. The time required for addition of the solution of the organic silicon compound is changed according to the amount of the solvent, but ordinarily, this time is selected in the range of from several minutes to several hours. Of course, for addition of the organic silicon compound, there may be adopted a method in which the organic silicon compound is directly added to the solution containing the precipitate therein. However, it is recommendable to avoid the adoption of this method, because it is industrially difficult to control the reaction.

The precipitate of the inorganic compound formed according to the above-mentioned method is separated and dried. The obtained inorganic compound comprises silica and $MO_{x/2}$ as the main constituents and has a surface area of at least 100 $m^2/g$. However, as is seen from the above-mentioned preparation method, in the obtained inorganic compound, it is construed that the surfaces of the particles are covered with a layer composed solely of silica or having a high silica content, and in the interiors of the particles, silica is combined to $MO_{x/2}$. The so-obtained inorganic compound has chemical properties similar to those of silica.

(4) In the above-mentioned method (3), seeds composed of silica are made present in the alkaline solvent as in the method (2), and then, the reaction is carried out in the same manner as in the method (3) to obtain the intended inorganic compound.

The method (4) is a combination of the above-mentioned methods (1), (2) and (3), and the reaction conditions as described with respect to these methods can be adopted. The inorganic compound obtained according to this method comprises a silica seed as the central core, a layer on the central core, which comprises as main constituents silica and an oxide of at least one metal selected from the group consisting of metals of the Groups I, II, III and IV of the Periodic Table, and a surface layer covering said layer, which is composed mainly of silica. The specific surface area of the inorganic compound is as large as at least 100 $m^2/g$, and a product having a spherical shape and a particle size of 0.1 to 1.0 $\mu m$ with such a particle size distribution that the standard deviation value is smaller that 1.30 can be obtained.

Each of the inorganic compounds obtained according to the methods (1) through (4) is composed mainly of a white or milky white amorphous powder, and a particulate product having a spherical shape is especially valuable. As pointed out hereinbefore, the so-obtained inorganic compound has a specific surface area of at least 100 $m^2/g$. Accordingly, the inorganic compound is advantageously used in fields where a large specific surface area is required, for example, as a catalyst, a catalyst carrier or an adsorbent.

The product provided according to the present invention includes an inorganic compound in which the amount of —OH groups present on the surface is drastically reduced by calcining the reaction product obtained according to any of the foregoing methods (1) through (4). The calcining method is not particularly critical, and calcining may be carried out at 200° to 1300° C. or a higher temperature according to known procedures. By calcining, the specific surface area of the inorganic compound is reduced, and if calcining is carried out at a temperature higher than 500° C., the specific surface area is reduced below 100 m²/g. When a spherical inorganic oxide is calcined, if the calcining temperature is higher than about 500° C., in many cases, the specific surface area is substantially equal to the specific surface area theoretically calculated from the particle size based on the supposition that the inorganic compound has a shape of a true sphere.

It sometimes happens that the structure of the powder is changed according to the calcining temperature. For example, an amorphous inorganic compound is kept amorphous even after calcining or a part of the amorphous structure is converted to a crystalline structure by calcining.

In order to improve the surface characteristics of the spherical inorganic compound of the present invention, various surface treatments can be adopted. For example, when this inorganic compound is used as a filler, in order to improve the moisture resistance or the dispersibility into a resin, the uncalcined or calcined spherical particles are treated with a silane such as dimethyldichlorosilane to block the silanol groups on the surfaces of the spherical particles. For this silane treatment, there can also be used a silane coupling agent such as γ-aminopropyltrimethoxysilane and a silane containing an ethylenically unsaturated group acting as an active point for graft polymerization, such as γ-methacryloxy-propyltrimethoxysilane.

The inorganic compound obtained by calcining has excellent properties and it is advantageously used, for example, as a filler for a dental material.

A dental restorative material comprising the inorganic compound of the present invention as a filler will now be described.

For example, an amorphous, spherical inorganic compound having a particle size of 0.1 to 1.0 μm and comprising as main constituents silica and an oxide of at least one metal selected from the group consisting of metals of the Groups I, II, III and IV of the Periodic Table, which is capable of combining with silica, said inorganic compound being prepared according to any of the foregoing methods, is incorporated alone and/or in the form of a composite resin filler containing said inorganic compound into a polymerizable vinyl monomer to form a dental restorative material.

As the composite resin filler containing said inorganic compound, there is preferably used a product obtained by mixing the inorganic compound with a vinyl monomer such as described below, adding a catalyst such as a peroxide or azo compound to the mixture, polymerizing the mixture and, if necessary, pulverizing the resulting polymer to an appropriate particle size.

One component of the dental restorative material is a polymerizable vinyl monomer. The kind of the vinyl monomer is not particularly critical and any of known vinyl monomers customarily used for dental materials may be used. As a typical instance of the vinyl monomer is a polymerizable vinyl monomer having an acryl group and/or a methacryl group. As the vinyl monomer having an acryl group and/or a methacryl group, there can be mentioned, for example, 2,2-bis[4-(2-hydroxy-3-methacryloxy phenyl]propane, methyl methacrylate, bis-methacryloxyphenyl-propane, triethylene glycol dimethacrylate, diethylene glycol dimethacrylate, tetramethylol acrylate, tetramethylol-methane trimethacrylate, trimethylol-ethane trimethacrylate and tetramethylol-methane tetramethyacrylate. Furthermore, there may be used vinyl monomers having a urethane structure, which are represented by the following structural formula:

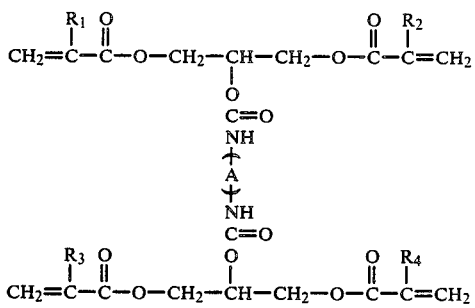

wherein $R_1$, $R_2$, $R_3$ and $R_4$, which may be the same or different, stand for H or $CH_3$ and —(—A—)— is preferably —(—$CH_2$—)$_6$—,

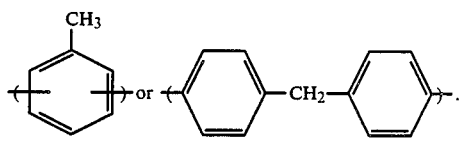

These vinyl monoers are known as component of dental materials and may be used singly or in combination.

When the inorganic compound of the present invention is used as a filler for the above-mentioned dental restorative material, there is preferably adopted a method in which a pasty mixture comprising the inorganic compound, the polymerizable vinyl monomer and a polymerization promoter such as a tertiary amine compound and a pasty mixture comprising the inorganic compound, the polymerizable vinyl monomer and a polymerization initiator, for example, an organic peroxide such as benzoyl peroxide are prepared in advance, and just before the restoration operation, both the mixtures are combined and kneaded together to effect curing. The composite resin obtained by curing the above-mentioned dental restorative material is comparable to conventional products in the mechanical strength characteristics such as the compressive strength and its is advantageous in various points. For example, the abrasion resistance and surface smoothness are excellent, the surface hardness is high, the surface polishing can be accomplished very easily, and the transparency is highly improved. The reasons why such excellent characteristics are manifested have not yet been elucidated completely. However, we now construe that the reasons may probably be as follows.

In the first place, since the inorganic compound having a spherical particle shape and such a uniform particle size that the deviation value of the particle size distribution is smaller than 1.30 is used, the inorganic compound is filled more uniformly and more densely in the composite resin obtained by curing than in the case where a conventional filler which is not uniform in the shape and has a broad particle size distribution is used.

In the second place, since the particle size of the inorganic compound is in the range of 0.1 to 1.0 μm, the polished surface of the composite resin obtained by curing is much smoother than in the case where a conventional inorganic filler having a particle size of scores of microns is used, and since the total specific surface area of the inorganic compound as the filler is smaller than that of a conventional ultra-fine filler composed mainly of ultra-fine particles having a particle size of scores of nanometers, the amount packed of the filler can be increased under conditions ensuring an appropriate operation adaptability.

In addition to the foregoing characteristics due to the specific shape, the filler according to the present invention has such a characteristic that the refractive index of the filler can easily be made in agreement with that of a polymer of a vinyl monomer, and if the refractive index of the filler is made in agreement with that of the polymer of the vinyl monomer, it is possible to obtain a composite resin which is especially excellent in the transparency.

In the restorative material obtained by incorporating the specific inorganic compound of the present invention into a polymerizable vinyl monomer, the above-mentioned unexpected merits can be attained. These merits are exerted by the polymerizable vinyl monomer component and the specific inorganic compound in the restorative material, but other additive components customarily used for dental restorative materials may be added according to need. As typical instances of these additives, there can be mentioned polymerization inhibitors, coloring pigments for color matching and ultraviolet ray absorbents.

The present invention will now be described in detail with reference to the following Examples that by no means limit the scope of the invention.

The properties mentioned in the Examples were determined according to the following methods unless otherwise indicated.

(1) Refractive Index:

A solvent having the same refractive index as that of a sample of the inorganic compound was prepared, and the refractive index of the solvent was designated as that of the sample. More specifically, the sample was suspended in a solvent and a solvent composition providing a suspension seen transparent with the naked eye was prepared. Pentane, hexane, cyclohexane, toluene, styrene and methylene iodide were used for forming a transparent solvent composition. The refractive index of the solvent was measured by an Abbe refractometer.

(2) Number of Surface —OH Groups:

At first, 2.00 g (W) of a sample of the inorganic compound was weighed and charged in an Erlenmeyer flask having a capacity of 100 ml, and 80 ml of a 0.05N aqueous solution of NaOH was added. The flask was sealed by a rubber plug and the content was allowed to stand with stirring for 12 hours. Then, the inorganic compound was separated from the solution by a centrifugal separator, and 10 ml of the solution was sampled by a pipet and subjected to neutralization titration with a 0.05N aqueous solution of HCl. The amount of the aqueous solution of HCl required for neutralization was designated as A ml. The above procedures were repeated without incorporating the sample, and the amount of the aqueous solution of HCl required for neutralization is designated as B ml. The amount (X millimole/g) of the surface —OH groups per unit weight of the inorganic compound was calculated according to the following formula:

$$X = \frac{(B - A) \times 0.05 \times 8}{W}$$

(3) Specific Gravity:

The specific gravity was measured by a pycnometer.

(4) Particle Size and Value of Standard Deviation Value of Particle Size Deviation:

A photograph of a sample powder was taken by using a scanning type electron microscope, and the number (n) of particles observed in the unit visual field of the photograph and the particle size (diameter, $x_i$) were determined. The standard deviation value was calculated according to the following formula:

$$\text{Standard Deviation Value} = \frac{\overline{x} + \delta_{n-1}}{\overline{x}}$$

wherein:

$$x = \frac{\sum_{i=1}^{n} x_i}{n} \text{ (number average particle size)}$$

$$\delta_{n-1} = \sqrt{\frac{\sum_{i=1}^{n} (x_i - x)^2}{n - 1}}$$

(5) Specific Surface Area:

The specific surface area was measured according to the principle of the BET method by using a prompt surface measuring apparatus (Model SA-1000 supplied by Shibata Kagaku Kiki Kogyo K.K.).

(6) Preparation of Restorative Material and Method of Curing Thereof:

An agate mortar was charged with an inorganic compound surface-treated with γ-methacryloxypropyl-trimethoxysilane and a vinyl monomer at a predetermined ratio, and they were sufficiently kneaded to form a homogeneous paste. The paste was divided into two equal portions, and a polymerization promotor was sufficiently mixed with one portion of the paste (paste A), while an organic peroxide catalyst was sufficiently mixed with the other portion of the paste (paste B). Then, equal amounts of the pastes A and B were kneaded for 30 seconds, and the mixture was packed in a mold frame and cured.

(7) Compressive Strength:

The pastes A and B were mixed and polymerized to form a columnar specimen having a diameter of 6 mm and a height of 12 mm at room temperature for 30 minutes, and the polymerization product was immersed in water at 37° C. for 24 hours. This specimen was attached to a testing machine (Model UTM-5T supplied by Toyo Baldwin) and the compressive strength was measured at a cross-head speed of 10 mm/min.

(8) Flexural Strength:

The pastes A and B were mixed and polymerized to form a trapezoidal specimen having a size of 2 mm×2 mm×25 mm at room temperature for 30 minutes, and the polymerization product was immersed in water at 37° C. for 24 hours. The bending test was carried out by using a bending tester having a distance of 20 mm between fulcra, which was attached to a testing machine (Model UTM-5T supplied by Toyo Baldwin), and the cross-head speed was 0.5 mm/min.

(9) Wear Depth and Surface Roughness by Toothbrush:

The pastes A and B were mixed and polymerized to form a plate-like specimen having a size of 1.5 mm × 10 mm × 10 mm at room temperature for 30 minutes, and the polymerization product was immersed in water at 37° C. for 24 hours. The specimen was rubbed along a length of 1500 m under a load of 400 g by a toothbrush with toothpaste, and then the surface roughness was measured by a surface roughness meter (Surfcom A-100). The ten point height of irregularities was calculated. The wear depth was determined by dividing the weight of wearing loss by the density of the sample resin.

(10) Surface Hardness:

The pastes A and B were mixed and polymerized to form a disc-like specimen having a size of 2.5 mm × 10 mm at room temperature for 30 minutes, and the polymerization product was immersed in water at 37° C. for 24 hours. The surface hardness was measured by using a microbrinell hardness tester.

Incidentally, in Tables 1 through 19 given hereinafter, the calcining time was 4 hours unless otherwise indicated.

The abbreviations used in the Examples are as follows.

AM: amorphous
AN: anatase
AM+AN: mixture of amorphous and anatase portions
AM+H: mixture of amorphous zirconia and tetragonal zirconia
IPA: isopropanol
MeOH: methanol
BuOH: butanol
bis-GMA: 2,2-bis[4-(2-hydroxy-3-methacryloxyphenyl)]propane
bis-MPP: di-(4-methacryloxyethoxyphenyl)propane
TEGDMA: triethylene glycol dimethacrylate
DEGDMA: diethylene glycol dimethacrylate
TMPT: trimethylolpropane triacrylate
TMM-3M: tetramethylolmethane triacrylate
TMM-4M: tetramethylolmethane tetraacrylate
NPG: neopentyl glycol dimethacrylate
U-4HMA:

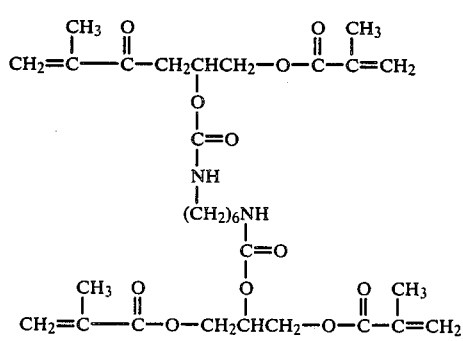

U-4TMA:

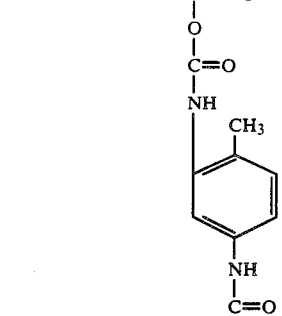

U-4BMA:

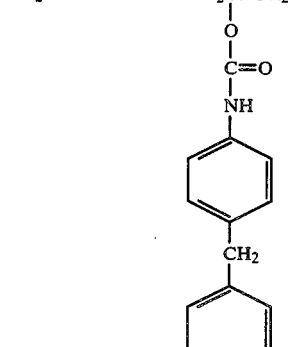

EXAMPLE 1

In 1.0 l of methanol were dissolved 208 g of tetraethyl silicate [Si(OC$_2$H$_5$)$_4$, Ethyl Silicate 28 supplied by Nippon Calcoat Kagaku] and 5.4 g of sodium methylate, and the solution was heated and refluxed for 30 minutes and cooled to room temperature to form a mixed solution. A glass vessel equipped with a stirrer and having an inner capacity of 10 l was charged with 2.5 l of methanol, and 500 g of aqueous ammonia (having a concentration of 25% by weight) was added thereto to form an ammoniac methanol solution and the above-mentioned mixed solution of tetraethyl silicate and sodium methylate was added to this solution with stirring over a period of about 2 hours while maintaining the temperature of the liquid mixture at 20° C. Within several minutes from the point of initiation of the addition, the liquid reaction mixture come to have a milky white color. After completion of the addition, the mixture was further stirred for 1 hour, and the solvent was removed from the milky white liquid reaction mixture by an evaporator and the residue was dried under reduced pressure at 80° C. to obtain a milky white powder.

When the powder was observed by scanning electron microscope photography, it was found that the powder had a spherical shape and a particle size of 0.20 to 0.35 μm and that the standard deviation value of the particle size was 1.07. The specific surface area as determined according to the BET method was 120 m²/g.

In the X-ray analysis, a gentle mountain-like absorption with the point of $2\theta = 25°$ being as the center was observed, and it was confirmed that the powder had an amorphous structure.

The thermal change and weight change were measured by a differential thermal analyzer and a thermobalance. It was found that endothermic reaction and weight loss considered to be due to dehydration were caused at about 100° C., and exothermic reaction and weight loss were observed at about 500° to about 600° C. and at higher temperatures of up to 1000° C., no thermal change or no weight change was observed.

After the powder had been calcined at 700° C. for 4 hours, the specific surface area of the powder was 14 m²/g, the specific gravity was 2.20 and the refractive index was from 1.45 to 1.46, and in the X-ray analysis, a gentle mountain-like absorption with the point of $2\theta = 21.5°$ being as the center was observed, and it was construed that the powder was amorphous. The $Na_2O$ content as determined by the fluorescent X-ray analysis was in agreement with the value calculated from the amount charged of the starting compound, and the yield was in agreement with the calculated value. The found $Na_2O$ content of the powder was 9.1 mole % (the calculated value was 9.1 mole %), and the measured value of the yield of the powder was 65.0 g (the calculated value was 66.3 g).

EXAMPLE 2

A solution formed by dissolving 208 g of the same tetramethyl silicate as used in Example 1 in 1.2 l of methanol was mixed with a solution of 31.1 g of barium bis-isopentoxide in 0.7 l of isoamyl alcohol. The mixed solution was refluxed at about 90° C. for 30 minutes in a dry nitrogen atmosphere, and the solution was cooled to room temperature to form a mixed solution of tetraethyl silicate and barium bis-isopentoxide.

In the same reaction vessel as used in Example 1, the same ammoniac methanol solution as used in Example 1 was prepared. Then, a solution of 4.0 g of tetraethyl silicate in 100 ml of methanol as the organic silicon compound solution for formation of silica seeds was added to the ammoniac methanol solution with stirring over a period of about 5 minutes, and when the liquid reaction mixture became slightly milky white within 5 minutes from the point of completion of the addition, the above-mentioned mixed solution was added to the liquid reaction mixture with stirring at 20° C. over a period of about 2 hours. With addition of the mixed solution, the suspension became milky white. After completion of the addition, the mixture was further stirred for 1 hour, and the solvent was removed from the milky white liquid reaction mixture by an evaporator. The residue was dried under reduced pressure at 80° C. to obtain a milky white powder. From the results of the observation of a scanning type electron microscope photograph, it was found that the powder had a spherical shape and a particle size of 0.25 to 0.35 μm. The standard deviation value of the particle size was 1.12. The specific surface area determined according to the BET method was 110 m²/g. In the X-ray analysis, a gentle mountain-like absorption with the point of $2\theta = 25°$ being as the center was observed, and it was confirmed that the powder had an amorphous structure.

When the thermal change and weight change were measured by a differential thermal analyzer and a thermobalance, endothermic reaction and weight loss considered to be due to dehydration were observed at about 100° C., and exothermic reaction and weight loss were observed at about 250° to about 550° C. At higher temperatures of up to 1000° C., no thermal change or no weight change was observed.

The specific surface area of the powder after 4 hours' calcining at 1000° C. was 12 m²/g, the specific gravity was 2.42 and the refractive index was from 1.52 to 1.53. In the X-ray analysis, a gentle mountain-like absorption with the point of $2\theta = 25°$ being as the center was observed, and it was confirmed that the powder was amorphous. The BaO content determined by the fluorescent X-ray analysis was in agreement with the value calculated from the amount of the charge, and the yield was in agreement with the value calculated from the amount of the charge. The found BaO content of the powder was 8.9 mole % (the calculated value was 8.9 mole %), and the measured value of the yield of the powder was 77.0 g (the calculated value was 78.2 g).

EXAMPLE 3

In 0.4 l of methanol were dissolved 3.6 g of water and 208 g of the same tetraethyl silicate as used in Example 1, and hydrolysis was carried out by stirring the solution at 60° C. for 2 hours. Then, a solution of 24.6 g of aluminum tris-sec-butoxide in 1.0 l of isopropanol was added to the hydrolyzed solution with stirring to form a mixed solution of hydrolyzed tetraethyl silicate and aluminum tris-sec-butoxide.

A glass reaction vessel equipped with a stirrer and having an inner capacity of 10 l was charged with 2.5 l of methanol, and 500 g of aqueous ammonia (the concentration was 25% by weight) was added to form an ammoniac methanol solution. The above-mentioned mixed solution was added to the liquid reaction mixture with stirring over a period of about 2 hours while maintaining the liquid mixture at 20° C. With addition of the mixed solution, the suspension became milky white. Then, a solution of 104 g of tetraethyl silicate in 0.5 l of methanol was added to the liquid reaction mixture containing the precipitated reaction product with stirring over a period of about 3 hours. After completion of the addition, the mixture was further stirred for 1 hour, and the solvent was removed by the liquid reaction mixture by an evaporator and the residue was dried under reduced pressure at 80° C. to obtain a milky white powder. From the results of the observation of a scanning type electron microscope photograph, the powder had a spherical shape and the particle size was from 0.12 to 0.25 μm. The standard deviation value of the particle size of the powder was 1.15. The specific surface area as determined according to the BET method was 110 m²/g. In the X-ray analysis, a gentle mountain-like absorption with the point of $2\theta = 25°$ being as the center was observed, and it was confirmed that the powder had an amorphous structure.

The thermal change and weight change measured by a differential thermal analyzer and a thermobalance were similar to those observed in Example 1.

The specific surface area of the powder after 1 hour's calcining at 1000° C. was 19 m²/g, and the number of the surface —OH groups was 0.08 millimole/g. The specific gravity of this calcined powder was 2.59 and the refractive index was from 1.46 to 1.47. In the X-ray analysis, a gentle mountain-like absorption with the point of $2\theta=22°$ being as the center was observed, and it was confirmed that the powder had an amorphous structure.

The $Al_2O_3$ content as determined by the fluorescent X-ray analysis was in agreement with the value calculated from the amount of the charge and the yield of the powder was in agreement with the value calculated from the amount of the charge. The found value of the $Al_2O_3$ content of the powder was 6.3 mole % (the calculated value was 6.3 mole %), and the measured value of the yield of the powder was 99.5 g (the calculated value was 100.3 g).

EXAMPLE 4

In 1.2 l of methanol were dissolved 5.4 g of water and 208 g of the same tetraethyl silicate as used in Example 1, and the solution was hydrolyzed at 60° C. for about 2 hours with stirring. The hydrolyzed solution was added to a solution of 54.0 g of tetrabutyl titanate [Ti(O—n—$C_4H_9$)$_4$ supplied by Nippon Soda] in 0.5 l of isopropanol with stirring to form a mixed solution of hydrolyzed tetraethyl silicate and tetrabutyl titanate. Then, in the same reaction vessel as used in Example 1, the same ammoniac methanol solution as used in Example 1 was prepared, and a solution of 4.0 g of tetraethyl silicate in 100 ml of methanol as an organic silicon compound solution for formation of silica seeds was added to the ammoniac methanol solution with stirring over a period of about 5 minutes. When the liquid reaction mixture became slightly milky white after passage of 5 minutes from the point of completion of the addition, the above-mentioned mixed solution was added to the liquid reaction mixture with stirring over a period of about 2 hours while maintaining the liquid reaction mixture at 20° C. to precipitate a reaction product. Then, a solution of 104 g of tetraethyl silicate in 0.5 l of methanol was added to the liquid reaction mixture containing the precipitated reaction product over a period of about 2 hours. The liquid reaction mixture was stirred for 1 hour after completion of the addition, and the solvent was removed from the milky white liquid reaction mixture by an evaporator. The residue was dried under reduced pressure at 80° C. to obtain a milky white powder.

When the powder was observed by scanning type electron microscope photography, it was found that the powder had a spherical shape and a particle size of 0.12 to 0.25 μm and that the standard deviation value of the particle size was 1.10. In the X-ray analysis, a gentle mountain-like absorption with the point of $2\theta=25.5°$ being as the center was observed, and it was confirmed that the powder had an amorphous structure. The specific surface area as determined according to the BET method was 120 $m^2/g$.

The thermal change and weight change were measured by a differential thermal analyzer and a thermobalance. It was found that endothermic reaction and weight loss considered to be due to dehydration were caused at about 100° C., and exothermic reaction and weight loss were observed at about 500° to about 600° C. and at higher temperatures of up to 1000° C., no thermal change or no weight change was observed.

The specific surface area of the powder after 4 hours' calcining at 1000° C. was 20 $m^2/g$, and the number of the surface —OH groups was 0.08 millimole/g. The specific gravity of this calcined powder was 2.40 and the refractive index was 1.53 to 1.54. In the X-ray analysis, a gentle mountain-like absorption with the point of $2\theta=22°$ being as the center and a small absorption based on titanium oxide of the anatase type were observed, and it was confirmed that the powder was a mixture of amorphous and crystalline portions.

In the infrared absorption spectrum of the powder, an absorption band based on the Si—O—Ti group was observed at 950 $cm^{-1}$. From the results of the fluorescent X-ray analysis, it was confirmed that the ratio of Si and Ti was in agreement with the ratio of Si and Ti in the charge and the yield was in agreement with the value calculated from the amount of the charge. From the foregoing results, it was confirmed that the powder had a spherical inorganic compound having an amorphous structure, which comprised 9.0 mole % of $TiO_2$ containing a minute amount of $TiO_2$ of the anatase type and 81.0 mole % of $SiO_2$.

EXAMPLES 5 THROUGH 10

The procedures of Example 4 were repeated in the same manner except that the composition of the organic silicon compound solution for formation of silica seeds and the composition of the organic silicon compound solution to be added after precipitation of the reaction product were changed as shown in Table 1. The obtained results are shown in Table 1. From the same observation as conducted in Example 4, it was confirmed that all of the obtained inorganic compounds were spherical.

TABLE 1

| Example No. | Composition of Organic Silicon Compound Solution for Formation of Silica Seeds | | Composition of Organic Silicon Compound Solution Added after Precipitation of Reaction Product | |
|---|---|---|---|---|
| | Organic Silicon Compound (g) | Alcohol (l) | Organic Silicon Compound (g) | Alcohol (l) |
| 5 | $Si(OC_2H_5)_4$ 16.0 | methanol 0.1 | ethyl silicate 40[1] 4.0 | methanol 0.2 |
| 6 | $Si(OC_2H_5)_4$ 32.0 | ethanol 0.2 | $Si(OC_2H_5)_4$ 8.0 | methanol 0.2 |
| 7 | $Si(OC_2H_5)_4$ 128.0 | methanol 0.5 | $Si(OC_2H_5)_4$ 8.0 | ethanol 0.2 |
| 8 | $Si(OC_2H_5)_4$ 4.0 | methanol 0.1 | $Si(OC_2H_5)_4$ 208 | methanol 1.0 |
| 9 | $Si(OC_2H_5)_4$ 4.0 | isopropanol 0.1 | $Si(OC_2H_5)_4$ 300 | methanol 1.0 |
| 10 | ethyl silicate 40[1] 4.0 | methanol 0.1 | $Si(OC_2H_5)_4$ 208 | methanol 1.0 |

| Characteristics of Inorganic Compound | | | |
|---|---|---|---|
| Specific | Particle | Standard | Number of[2] |

TABLE 1-continued

| Example No. | Calcining Temperature (°C.) | Surface Area (m²/g) | X-Ray Analysis | Size Range (μm) | Deviation Value | Refractive Index | Specific[2] Gravity | Surface —OH Groups (millimole/g) |
|---|---|---|---|---|---|---|---|---|
| 5 | 200 | 130 | AM | 0.10~0.20 | 1.05 | 1.53~1.54 | 1.35 (200° C.) | 1.30 (200° C.) |
|   | 1000 | 20 | AM + AN |  |  |  | 2.50 (1000° C.) | 0.10 (1000° C.) |
| 6 | 200 | 110 | AM | 0.10~0.20 | 1.08 | 1.53~1.54 | 1.40 (200° C.) | — |
|   | 1000 | 20 | AM + AN |  |  |  | 2.10 (1000° C.) |  |
| 7 | 200 | 110 | AM | 0.12~0.20 | 1.10 | 1.53~1.54 |  | — |
|   | 1000 | 18 | AM + AN |  |  |  | 2.30 (1000° C.) |  |
| 8 | 200 | 120 | AM | 0.12~0.25 | 1.08 | 1.53~1.54 |  | — |
|   | 1000 | 15 | AM + AN |  |  |  | 2.30 (1000° C.) |  |
| 9 | 200 | 120 | AM | 0.12~0.25 | 1.10 | 1.53~1.54 |  | 1.10 (300° C.) |
|   | 1000 | 20 | AM + AN |  |  |  | 2.40 (1000° C.) | 0.08 (1000° C.) |
| 10 | 200 | 120 | AM | 0.15~0.25 | 1.15 | 1.53~1.54 | 1.60 (200° C.) | 1.60 (200° C.) |
|   | 1000 | 20 | AM + AN |  |  |  | 2.40 (1000° C.) | 0.08 (1000° C.) |

Note
[1]Product supplied by Nippon Colcoat Kagaku
[2]Each parenthesized value indicates the calcining temperature (the calcining time was 4 hours)

EXAMPLES 11 THROUGH 18

The procedures of Example 4 were repeated in the same manner except that the alcohol of the ammoniac methanol was changed to isopropanol and the composition of the reactants in the mixed solution was changed as shown in Table 2. The obtained results are shown in Table 2. From the results of the same observation as conducted in Example 4, it was confirmed that all of the obtained inorganic compounds were spherical.

In Example 11, an aqueous solution of hydrochloric acid having a concentration of $20 \times 10^{-3}$ mole/l was used as water of the mixed solvent, and the mixed solution was prepared by mixing 54 ml of this aqueous solution of hydrochloric acid with the tetraethyl silicate solution, stirring the mixture for 30 minutes and adding the tetrabutyl titanate solution to the mixture.

TABLE 2

| | Composition of Starting Compounds in Mixed Solution | | | | Characteristics of Inorganic Compound | | | | | |
|---|---|---|---|---|---|---|---|---|---|---|
| Example No. | Si(OC₂H₅)₄ (g) | Water (g) | Ti(O—nC₄H₉)₄ (g) | Isopropanol (l) | Calcining Temperature (°C.) | Specific Surface Area (m²/g) | X-Ray Analysis | Particle Size Range (μm) | Standard Deviation Value | Refractive Index |
| 11 | 208 | 7.2 | 72.0 | 1.0 | 200 | 120 | AM | 0.13~0.30 | 1.10 | 1.56~1.57 |
|  |  |  |  |  | 1000 | 24 | AM + AN |  |  |  |
| 12 | 208 | 9.0 | 90.0 | 1.0 | 200 | 130 | AM | 0.12~0.32 | 1.20 | 1.60~1.61 |
|  |  |  |  |  | 1000 | 25 | AM + AN |  |  |  |
| 13 | 208 | 10.8 | 108.0 | 2.0 | 200 | 130 | AM | 0.10~0.25 | 1.15 | 1.62~1.63 |
|  |  |  |  |  | 1000 | 30 | AM + AN |  |  |  |
| 14 | 208 | 5.4 | 36.0 | 1.0 | 200 | 110 | AM | 0.12~0.21 | 1.12 | 1.49~1.51 |
|  |  |  |  |  | 1000 | 27 | AM + AN |  |  |  |
| 15 | 208 | 3.2 | 18.0 | 1.0 | 200 | 110 | AM | 0.16~0.27 | 1.10 | 1.42~1.43 |
|  |  |  |  |  | 1000 | 27 | AM |  |  |  |
| 16 | 208 | 14.4 | 25.0 | 1.0 | 200 | 120 | AM | 0.11~0.21 | 1.07 | 1.45~1.46 |
|  |  |  |  |  | 1000 | 28 | AM |  |  |  |
| 17 | 208 | 54 | 1.8 | 1.0 | 200 | 110 | AM | 0.15~0.30 | 1.12 | 1.37~1.38 |
|  |  |  |  |  | 1000 | 30 | AM |  |  |  |
| 18 | 208 | 5.4 | 54.0 | 1.5 | 200 | 110 | AM | 0.21~0.32 | 1.05 | 1.53~1.54 |
|  |  |  |  |  | 1000 | 10 | AM + AN |  |  |  |

EXAMPLES 19 THROUGH 21

The procedures of Example 4 were repeated in the same manner except that the alcohol of the ammoniac methanol was changed to isopropanol and the composition of the reactants in the mixed solution was changed as shown in Table 3. The obtained results are shown in Table 3. From the results of the same observation as conducted in Example 4, it was confirmed that all of the obtained inorganic compounds were spherical.

TABLE 3

| | Composition of Starting Compounds in Mixed Solution | | | | Characteristics of Inorganic Compound | | | | | |
|---|---|---|---|---|---|---|---|---|---|---|
| Example No. | Organic Silicon Compound (g) | Water (g) | Ti(O—nC₄H₉)₄ (g) | Alcohol (l) | Calcining Temperature (°C.) | Specific Surface Area (m²/g) | X-Ray Analysis | Particle Size Range (μm) | Standard Deviation Value | Refractive Index |
| 19 | Si(O—nC₃H₇)₄ 264 | 5.4 | 54.0 | IPA = 0.5 MeOH = 0.5 | 200 1000 | 120 10 | AM AM + AN | 0.16~0.26 | 1.10 | 1.53~1.54 |
| 20 | Si(O—nC₄H₉)₄ 320 | 5.4 | 54.0 | IPA = 0.5 MeOH = 0.5 | 200 1000 | 110 10 | AM AM + AN | 0.20~0.30 | 1.08 | 1.53~1.54 |
| 21 | ethyl silicate 40[1] 145 | 5.4 | 34.0 | IPA = 0.5 MeOH = 0.5 | 200 1000 | 110 24 | AM AM + AN | 0.12~0.24 | 1.15 | 1.53~1.54 |

Note
[1]See Table 1.

EXAMPLES 22 THROUGH 29

The procedures of Example 4 were repeated in the same manner except that the composition of the ammoniac alcohol was changed as shown in Table 4. The obtained results are shown in Table 4. From the results of the same measurement as conducted in Example 4, it was confirmed that all of the obtained inorganic compounds were spherical.

EXAMPLES 30 THROUGH 37

The procedures of Example 4 were repeated in the same manner except that the composition of the starting compounds in the mixed solution was changed as shown in Table 5. The obtained results are shown in Table 5. From the results of the same observation as conducted in Example 4, it was confirmed that all of the obtained inorganic compounds were spherical.

TABLE 4

| | Ammoniac Alcohol | | | | Characteristics of Inorganic Compound | | | | | |
|---|---|---|---|---|---|---|---|---|---|---|
| Example No. | Ammonia (g) | Water (g) | Alcohol (l) | Liquid Temperature (°C.) | Calcining Temperature (°C.) | Specific Surface Area ($m^2/g$) | X-Ray Analysis | Particle Size Range ($\mu m$) | Standard Deviation Value | Refractive Index |
| 22 | 125 | 375 | MeOH = 1.25 IPA = 1.25 | 20 | 80 1000 | 120 18 | AM AM + AN | 0.24~0.40 | 1.09 | 1.53~1.54 |
| 23 | 125 | 375 | IPA = 2.5 | 20 | 80 1000 | 110 8 | AM AM + AN | 0.30~0.40 | 1.06 | 1.53~1.54 |
| 24 | 125 | 375 | EtOH = 2.5 | 20 | 80 1000 | 130 15 | AM AM + AN | 0.30~0.40 | 1.06 | 1.53~1.54 |
| 25 | 125 | 375 | BuOH = 2.5 | 20 | 80 1000 | 110 10 | AM AM + AN | 0.35~0.50 | 1.06 | 1.53~1.54 |
| 26 | 125 | 375 | MeOH = 2.5 | 10 | 80 1000 | 110 8 | AM AM + AN | 0.12~0.23 | 1.11 | 1.53~1.54 |
| 27 | 125 | 375 | MeOH = 2.5 | 30 | 80 1000 | 110 10 | AM AM + AN | 0.10~0.20 | 1.11 | 1.53~1.54 |
| 28 | 100 | 300 | IPA = 2.5 | 25 | 80 1000 | 120 15 | AM AM + AN | 0.26~0.47 | 1.08 | 1.53~1.54 |
| 29 | 80 | 375 | IPA = 2.5 | 20 | 80 1000 | 110 16 | AM AM + AN | 0.25~0.40 | 1.09 | 1.53~1.54 |

Incidentally, in Example 35, the mixed solution was refluxed at 80° C. for 1 hour, the temperature was returned to room temperature, and the mixed solution was then added to the ammoniac alcohol solution.

TABLE 5

| | Composition of Starting Compounds in Mixed Solution | | | |
|---|---|---|---|---|
| Example No. | $Si(OC_2H_5)_4$ (g) | Water (g) | Organic Compound of Metal of Group IV of Periodic Table (g) | Isopropanol (l) |
| 30 | 208 | 5.4 | Ti(O—isoC$_3$H$_7$)$_4$ 42.6 | 1.0 |
| 31 | 208 | 5.4 | Ti(O—isoC$_3$H$_7$)$_2$ [OC(CH$_3$)CHCOCH$_3$]$_2$ 72.8 | 1.0 |
| 32 | 208 | 5.4 | Ti(OCH$_2$CH(C$_2$H$_5$)C$_4$H$_9$)$_4$ 84.6 | 1.0 |
| 33 | 208 | 5.4 | Ti(O—nC$_4$H$_9$)$_2$ (OCOC$_{17}$H$_{35}$) 82.6 | 1.0 |
| 34 | 208 | 1.8 | Zr(O—nC$_4$H$_9$)$_4$ 38.3 | 0.5 |
| 35 | 208 | 0 | Zr(O—nC$_4$H$_9$)$_4$ 19.1 | 1.0 |
| 36 | 208 | 3.6 | Ge(O—nC$_4$H$_9$)$_4$ 36.5 | 1.0 |
| 37 | 208 | 3.6 | Sn(O—nC$_4$H$_9$)$_4$ 25.0 | 1.0 |

| | Characteristics of Inorganic Compound | | | | | |
|---|---|---|---|---|---|---|
| Example No. | Calcining Temperature (°C.) | Specific Surface Area ($m^2/g$) | X-Ray Analysis | Particle Size Range ($\mu m$) | Standard Deviation Value | Refractive Index |
| 30 | 80 1000 | 130 20 | AM AM + AN | 0.13~0.30 | 1.10 | 1.53~1.54 |
| 31 | 80 1000 | 120 10 | AM AM + AN | 0.50~0.90 | 1.10 | 1.53~1.54 |
| 32 | 80 1000 | 130 18 | AN AM + AN | 0.15~0.30 | 1.12 | 1.53~1.54 |
| 33 | 80 1000 | 130 18 | AM AM + AN | 0.15~0.34 | 1.10 | 1.53~1.54 |
| 34 | 80 1000 | 110 40 | AM AM + AH | 0.10~0.20 | 1.05 | 1.52~1.53 |
| 35 | 80 | 110 | AM | 0.10~0.20 | 1.18 | 1.45~1.46 |

TABLE 5-continued

|    | 1000 | 15  | AM |           |      |             |
|----|------|-----|----|-----------|------|-------------|
| 36 | 80   | 115 | AM | 0.22~0.32 | 1.05 | 1.46~1.48   |
|    | 1000 | 15  | AM |           |      |             |
| 37 | 80   | 120 | AM | 0.20~0.30 | 1.05 | 1.48~1.49   |
|    | 1000 | 16  | AM |           |      |             |

EXAMPLES 38 THROUGH 43

The procedures of Example 1 were repeated in the same manner except that the composition of the starting compounds in the mixed solution was changed as shown in Table 6. The obtained results are shown in Table 6. From transmission type electron microscope photographs, it was confirmed that all of the obtained inorganic compounds were spherical.

TABLE 6

| | Composition of Starting Compounds in Mixed Solution | | | Characteristics of Inorganic Compound | | | | | |
|---|---|---|---|---|---|---|---|---|---|
| Example No. | Si(OC$_2$H$_5$)$_4$ (g) | Organic Compound of Metal of Group I of Periodic Table (g) | Alcohol (l) | Calcining Temperature (°C.) | Specific Surface Area (m$^2$/g) | X-Ray Analysis | Particle Size Range (μm) | Standard Deviation Value | Refractive Index |
| 38 | 208 | NaOC$_2$H$_5$ | EtOH | 200 | 11 | AM | 0.15~0.25 | 1.10 | 1.45~1.46 |
|    |     | 6.8 | 2.0 | 750 | 15 | AM | | | |
| 39 | 208 | NaO—isoC$_3$H$_7$ | IPA | 200 | 125 | AM | 0.15~0.25 | 1.15 | 1.45~1.46 |
|    |     | 8.2 | 2.0 | 750 | 16 | AM | | | |
| 40 | 208 | KOCH$_3$ | MeOH | 200 | 110 | AM | 0.15~0.25 | 1.10 | 1.45~1.46 |
|    |     | 7.0 | 1.0 | 750 | 16 | AM | | | |
| 41 | 208 | KOC$_2$H$_5$ | MeOH | 200 | 110 | AM | 0.15~0.30 | 1.15 | 1.45~1.46 |
|    |     | 8.4 | 1.0 | 700 | 13 | AM | | | |
| 42 | 208 | LiOCH$_3$ | EtOH | 200 | 115 | AM | 0.15~0.25 | 1.10 | 1.45~1.46 |
|    |     | 3.8 | 1.2 | 750 | 15 | AM | | | |
| 43 | 208 | LiOC$_2$H$_5$ | EtOH | 200 | 120 | AM | 0.15~0.25 | 1.12 | 1.45~1.46 |
|    |     | 5.2 | 1.2 | 750 | 16 | AM | | | |

EXAMPLES 44 THROUGH 52

The procedures of Example 2 were repeated in the same manner except that the composition of the starting compounds in the mixed solution was changed as shown in Table 7, the obtained results were shown in Table 7. From the results of the same observation as conducted in Example 2, it was confirmed that all of the obtained inorganic compounds were spherical.

TABLE 7

| | Composition of Starting Compounds in Mixed Solution | | | Characteristics of Inorganic Compound | | | | | |
|---|---|---|---|---|---|---|---|---|---|
| Example No. | Si(OC$_2$H$_5$)$_4$ (g) | Organic Compound of Metal of Group III of Periodic Table (g) | Alcohol (l) | Calcining Temperature (°C.) | Specific Surface Area (m$^2$/g) | X-Ray Analysis | Particle Size Range (μm) | Standard Deviation Value | Refractive Index |
| 44 | 208 | Ba(OCH$_3$) | MeOH | 200 | 115 | AM | 0.10~0.35 | 1.20 | 1.52~1.53 |
|    |     | 19.9 | 2.0 | 1000 | 25 | AM | | | |
| 45 | 208 | Ba(OC$_2$H$_5$)$_2$ | EtOH | 200 | 120 | AM | 0.10~0.35 | 1.20 | 1.52~1.53 |
|    |     | 22.7 | 2.0 | 1000 | 23 | AM | | | |
| 46 | 208 | Ba(O—isoC$_3$H$_7$)$_2$ | IPA | 200 | 113 | AM | 0.10~0.35 | 1.15 | 1.52~1.53 |
|    |     | 25.5 | 2.0 | 1000 | 21 | AM . | | | |
| 47 | 208 | Mg(OCH$_3$)$_2$ | MeOH | 200 | 125 | AM | 0.15~0.35 | 1.02 | 1.51~1.52 |
|    |     | 8.6 | 1.0 | 700 | 13 | AM | | | |
| 48 | 208 | Mg(OC$_2$H$_5$)$_2$ | EtOH | 200 | 123 | AM | 0.15~0.35 | 1.06 | 1.51~1.52 |
|    |     | 11.4 | 1.2 | 700 | 12 | AM | | | |
| 49 | 208 | Ca(OCH$_3$)$_2$ | MeOH | 200 | 124 | AM | 0.15~0.30 | 1.03 | 1.50~1.51 |
|    |     | 10.2 | 1.1 | 700 | 10 | AM | | | |
| 50 | 208 | Ca(OC$_2$H$_5$)$_2$ | EtOH | 200 | 121 | AM | 0.15~0.30 | 1.09 | 1.50~1.51 |
|    |     | 13.0 | 1.3 | 700 | 11 | AM | | | |
| 51 | 208 | Sr(OCH$_3$)$_2$ | MeOH | 200 | 120 | AM | 0.15~0.35 | 1.05 | 1.49~1.50 |
|    |     | 15.0 | 1.5 | 700 | 13 | AM | | | |
| 52 | 208 | Sr(OC$_2$H$_5$)$_2$ | EtOH | 200 | 117 | AM | 0.15~0.35 | 1.10 | 1.49~1.50 |
|    |     | 17.8 | 2.0 | 700 | 12 | AM | | | |

EXAMPLES 53 THROUGH 60

The procedures of Example 3 were repeated in the same manner except that the composition of the starting compounds in the mixed solution was changed as shown in Table 8. The obtained results are shown in Table 8. From the results of the same observation as conducted in Example 1, it was confirmed that all of the obtained inorganic compounds were spherical.

Incidentally, in each of Examples 58 through 60, the mixed solution having a composition shown in Table 8 was heated and refluxed at 100° C. in a nitrogen atmosphere for 30 minutes, and it was then cooled to room temperature and used.

TABLE 8

| Example No. | Composition of Starting Compounds in Mixed Solution | | | | Characteristics of Inorganic Compound | | | | | |
|---|---|---|---|---|---|---|---|---|---|---|
| | $Si(OC_2H_5)_4$ (g) | Water (g) | Organic Compound of Metal of Group III of Periodic Table (g) | Alcohol (l) | Calcining Temperature (°C.) | Specific Surface Area ($m^2/g$) | X-Ray Analysis | Particle Size Range ($\mu m$) | Standard Deviation Value | Refractive Index |
| 53 | 208 | 3.6 | $Al(O-isoC_3H_7)_3$ 20.4 | IPA = 1.0 MeOH = 0.4 | 80 1000 | 120 22 | AM AM | 0.1~0.20 | 1.20 | 1.46~1.47 |
| 54 | 208 | 3.6 | $Al(O-nC_4H_9)(O-isoC_3H_7)_2$ 21.8 | IPA = 1.0 MeOH = 0.4 | 80 1000 | 115 19 | AM AM | 0.10~0.25 | 1.15 | 1.46~1.47 |
| 55 | 208 | 3.6 | $Al(O-nC_4H_9)_3$ 24.6 | IPA = 1.0 MeOH = 0.4 | 80 1000 | 121 20 | AM AM | 0.17~0.30 | 1.14 | 1.46~1.47 |
| 56 | 208 | 4.0 | $B(OC_2H_5)_3$ 15.1 | IPA = 1.0 MeOH = 0.4 | 80 700 | 103 18 | AM AM | 0.15~0.30 | 1.12 | 1.38~1.39 |
| 57 | 208 | 4.0 | $Y(O-isoC_3H_7)_3$ 29.6 | IPA = 1.0 MeOH = 0.4 | 80 700 | 105 18 | AM AM | 0.15~0.30 | 1.15 | 1.48~1.49 |
| 58 | 208 | 0 | $Al(O-isoC_3H_7)_3$ 20.4 | IPA = 1.0 | 80 1000 | 109 19 | AM AM | 0.12~0.22 | 1.19 | 1.46~1.47 |
| 59 | 208 | 0 | $Al(O-nC_4H_9)(O-isoC_3H_7)_2$ 21.8 | IPA = 1.0 | 80 1000 | 123 17 | AM AM | 0.12~0.25 | 1.19 | 1.46~1.47 |
| 60 | 208 | 0 | $Al(O-nC_4H_9)_3$ 24.6 | IPA = 1.0 | 80 1000 | 109 14 | AM AM | 0.12~0.25 | 1.14 | 1.46~1.47 |

EXAMPLE 61

In 0.2 l of methanol were dissolved 1.8 g of water and 104 g of tetraethyl silicate [$Si(OC_2H_5)_4$, Ethyl Silicate 28 supplied by Nippon Colcoat Kagaku], and hydrolysis was carried out by stirring this solution for about 2 hours at room temperature. A solution of 17.0 g of tetrabutyl titanate [$Ti(O-n-C_4H_9)_4$ supplied by Nippon Soda] in 1.0 l of isopropanol was added to the hydrolyzed solution with stirring to form a mixed solution (A) of hydrolyzed tetraethyl silicate and tetrabutyl titanate. Then, 7.8 g of barium bisisopentoxide and 104 g of tetraphenyl silicate were dissolved in 1.0 l of methanol, and the solution was refluxed at 90° C. in a nitrogen atmosphere for 30 minutes and the temperature was returned to room temperature to form a mixed solution (B). The mixed solution (A) was mixed with the mixed solution (B) at room temperature to form a mixed solution (C).

A glass reaction vessel equipped with a stirrer and having an inner capacity of 10 l was charged with 2.5 l of methanol, and 500 g of aqueous ammonia (having a concentration of 25% by weight) was added to form an ammoniac solution. The above-mentioned mixed solution (C) was added to the so-formed solution with stirring over a period of about 4 hours while maintaining the liquid temperature at 20° C. Within several minutes from the point of initiation of the addition, the liquid reaction became milky white. After completion of the addition, the liquid reaction mixture was further stirred for 1 hour. The solvent was removed from the milky white liquid reaction mixture by an evaporator and the residue was dried under reduced pressure at 80° C. to form a milky white powder.

When the powder was observed by scanning type electron microscope photography, it was found that the powder had a spherical shape and a particle size of 0.12 to 0.26 $\mu m$ and that the standard deviation value of the particle size was 1.06. The specific surface area as determined according to the BET method was 130 $m^2/g$.

In the X-ray analysis, a gentle mountain-like absorption with the point of $2\theta=25°$ being as the center was observed, and it was confirmed that the powder had an amorphous structure.

The thermal change and weight change were measured by a differential thermal analyzer and a thermobalance. It was found that endothermic reaction and weight loss considered to be due to dehydration were caused at about 100° C., and exothermic reaction and weight loss were observed at about 200° to about 650° C. and at higher temperatures of up to 1000° C., no thermal change or no weight change was observed.

After the powder had been calcined at 800° C. for 2 hours, the specific surface area of the powder was 17 $m^2/g$, the specific gravity was 2.49 and the refractive index was 1.52 to 1.53, and in the X-ray analysis, a gentle mountain-like absorption was observed, and it was construed that the powder was amorphous. The $TiO_2$ and BaO contents as determined by the fluorescent X-ray analysis were in agreement with the values calculated from the amounts charged of the reactants, and the yield was in agreement with the calculated value. The found $TiO_2$ content of the powder was 4.7 mole % (the calculated value was 4.7 mole %), the found BaO content was 2.3 mole % (the calculated value was 2.3 mole %), and the measured value of the yield of the powder was 67.0 g (the calculated value was 67.9 g).

EXAMPLES 62 THROUGH 69

The procedures of Example 61 were repeated in the same manner except that the compositions of the organic silicon compound, organic metal compound and water in the mixed solutions were changed as shown in Table 9. The obtained results are shown in Table 9. From the results of the observation of scanning type electron microscope photographs, it was confirmed that all of the obtained inorganic compounds were spherical.

TABLE 9

| | Composition of Starting Compounds of Mixed Solutions | | | |
|---|---|---|---|---|
| | Mixed Solution (A) | | Mixed Solution (B) | |
| Example | $Si(OC_2H_5)_4$ | Organic Metal | $Si(OC_2H_5)_4$ | Organic Metal |

TABLE 9-continued

| No. | (g) | Water (g) | Compound (g) | (g) | Compound (g) |
|---|---|---|---|---|---|
| 62 | 104 | 1.8 | $Ti(OC_4H_9)_4$ 17.0 | 104 | $Sr(OCH_3)_2$ 7.5 |
| 63 | 104 | 1.8 | $Ge(OC_4H_9)_4$ 18.2 | 104 | $Ca(OCH_3)_2$ 5.1 |
| 64 | 104 | 0 | $Zr(OC_4H_9)_4$ 19.2 | 104 | $Ba(O—iso-C_5H_{11})_2$ 15.6 |
| 65 | 104 | 1.8 | $Ti(OC_4H_9)_4$ 17.0 | 104 | $NaOCH_3$ 2.7 |
| 66 | 104 | 1.8 | $Ti(OC_4H_9)_4$ 17.0 | 104 | $Al(O—sec-C_4H_9)_3$ 15.0 |
| 67 | 104 | 1.8 | $B(OC_2H_5)_3$ 6.8 | 104 | $Mg(OC_2H_5)_2$ 5.7 |
| 68 | 104 | 0 | $Al(O—sec-C_4H_9)_3$ 15.0 | 104 | $NaOCH_3$ 2.7 |
| 69 | 104 | 0 | $Mg(OC_2H_5)_2$ 5.7 | 104 | $NaOCH_3$ 2.7 |

| | Characteristics of Inorganic Compound | | | | | |
|---|---|---|---|---|---|---|
| Example No. | Calcining Temperature (°C.) | Specific Surface Area (m²/g) | X-Ray Analysis | Refractive Index | Specific Gravity | Particle Size Range (μm) | Standard Deviation Value |
| 62 | 200 | 120 | AM | — | — | 0.15~0.23 | 1.05 |
|    | 800 | 15  | AM | 1.54~1.55 | 2.79 | | |
| 63 | 200 | 120 | AM | — | — | 0.10~0.20 | 1.10 |
|    | 1000 | 16 | AM | 1.51~1.52 | 2.75 | | |
| 64 | 200 | 130 | AM | — | — | 0.10~0.25 | 1.20 |
|    | 1000 | 25 | AM | 1.50~1.51 | 2.90 | | |
| 65 | 200 | 115 | AM | — | — | 0.15~0.25 | 1.10 |
|    | 800 | 14 | AM | 1.50~1.51 | 2.58 | | |
| 66 | 200 | 130 | AM | — | — | 0.14~0.25 | 1.15 |
|    | 1000 | 40 | AM | 1.51~1.52 | 2.76 | | |
| 67 | 200 | 120 | AM | — | — | 0.15~0.25 | 1.10 |
|    | 800 | 15 | AM | 1.49~1.50 | 2.64 | | |
| 68 | 200 | 130 | AM | — | — | 0.10~0.25 | 1.25 |
|    | 1000 | 45 | AM | 1.48~1.49 | 2.57 | | |
| 69 | 200 | 115 | AM | — | — | 0.15~0.25 | 1.06 |
|    | 800 | 12 | AM | 1.43~1.44 | 2.55 | | |

EXAMPLE 70

In a glass reaction vessel equipped with a stirrer and having an inner capacity of 10 l, the same ammoniac methanol solution as used in Example 61 was prepared. Then, a solution of 4.0 g of tetraethyl silicate in 100 ml of methanol as the organic silicon compound solution for formation of silica seeds was added to the ammoniac methanol solution with stirring over a period of about 5 minutes, and when the liquid reaction mixture became slightly milky white within 5 minutes from the point of completion of the addition, the same mixed solution (C) as used in Example 6 was added to the liquid reaction mixture at 20° C. over a period of about 4 hours to precipitate a reaction product. Then, a solution of 104 g of tetraethyl silicate in 0.5 l of methanol was added to the liquid reaction mixture containing the precipitated reaction product with stirring over a period of about 2 hours. The liquid reaction mixture was further stirred for 1 hour after completion of the addition, and the solvent was removed from the milky white liquid reaction mixture by an evaporator. The residue was dried under reduced pressure at 80° C. to obtain a milky white powder.

From the results of the observation of a scanning type electron microscope photograph, the powder had a spherical shape and the particle size was 0.17 to 0.32 μm. The standard deviation value of the particle size of the powder was 1.05. In the X-ray analysis, a gentle mountain-like absorption with the point of $2\theta=25°$ being as the center was observed, and it was confirmed that the powder had an amorphous structure. The specific surface area as determined according to the BET method was 120 m²/g.

The thermal change and weight change measured by a differential thermal analyzer and a thermobalance were similar to those observed in Example 61.

The specific surface area of the powder after 4 hours' sintering at 800° C. was 14 m²/g, and the number of the surface —OH groups was 0.25 millimole/g. The specific gravity of this sintered powder was 2.44 and the refractive index was 1.51 to 1.52. In the X-ray analysis, a gentle mountain-like absorption with the point of $2\theta=22°$ being as the center was observed, and it was confirmed that the powder had an amorphous structure.

The ratio of Si, Ti and Ba as determined by the fluorescent X-ray analysis was in agreement with the value calculated from the amounts charged of the starting compounds. Furthermore, the yield was substantially in agreement with the value calculated from the amount charged of the starting compounds. Thus, it was confirmed that the product was a spherical inorganic compound having an amorphous structure, which comprised 3.1 mole % of $TiO_2$, 1.6 mole % of BaO and 95.3 mole % of $SiO_2$.

EXAMPLES 71 THROUGH 78

The procedures of Example 70 were repeated in the same manner except that the compositions of the starting compounds in the mixed solutions were charged as shown in Table 10. The obtained results are shown in Table 10. From the results of observation of scanning type electron microscope photographs, it was confirmed that all of the obtained inorganic compounds were spherical.

TABLE 10

Composition of Mixed Solutions

| Example No. | Mixed Solution (A) Si(OC$_2$H$_5$)$_4$ (g) | Water (g) | Organic Metal Compound (g) | Alcohol (l) | Mixed Solution (B) Si(OC$_2$H$_5$)$_4$ (g) | Organic Metal Compound (g) | Alcohol (l) |
|---|---|---|---|---|---|---|---|
| 71 | 104 | 1.8 | Ti(OC$_4$H$_9$)$_4$ 17.0 | MeOH = 0.2 IPA = 1.0 | 104 | Sr(OCH$_3$)$_2$ 7.5 | MeOH = 1.0 |
| 72 | 104 | 1.8 | Ge(OC$_4$H$_9$)$_4$ 18.2 | MeOH = 0.2 IPA = 1.0 | 104 | Ca(OCH$_3$)$_2$ 5.1 | MeOH = 1.0 |
| 73 | 104 | 1.8 | Zr(OC$_4$H$_9$)$_4$ 19.2 | MeOH = 0.2 IPA = 1.0 | 104 | Ba(O—iso-C$_5$H$_{11}$)$_2$ 15.6 | MeOH = 1.0 |
| 74 | 104 | 1.8 | Ti(OC$_4$H$_9$)$_4$ 17.0 | MeOH = 0.2 IPA = 1.0 | 104 | NaOCH$_3$ 2.7 | MeOH = 0.5 |
| 75 | 104 | 1.8 | Ti(OC$_4$H$_9$)$_4$ 17.0 | MeOH = 0.2 IPA = 1.0 | 104 | Al(O—sec-C$_4$H$_9$)$_3$ 15.0 | IPA = 1.0 |
| 76 | 104 | 1.8 | B(OC$_2$H$_5$)$_3$ 6.8 | MeOH = 0.2 MeOH = 0.5 | 104 | Mg(OC$_2$H$_5$)$_2$ 5.7 | MeOH = 0.7 |
| 77 | 104 | 0 | Al(O—sec-C$_4$H$_9$)$_3$ 15.0 | IPA = 1.0 | 104 | NaOCH$_3$ 2.7 | MeOH = 0.5 |
| 78 | 104 | 0 | Mg(OC$_2$H$_5$)$_2$ 5.7 | MeOH = 1.0 | 104 | NaOCH$_3$ 2.7 | MeOH = 0.5 |

Characteristics of Inorganic Compound

| Example No. | Calcining Temperature (°C) | Specific Surface Area (m$^2$/g) | X-Ray Analysis | Refractive Index | Specific Gravity | Particle Size Range (μm) | Standard Deviation Value |
|---|---|---|---|---|---|---|---|
| 71 | 200 | 115 | AM | — | — | 0.20~0.30 | 1.04 |
|    | 800 | 14 | AM | 1.54~1.55 | 2.78 | | |
| 72 | 200 | 115 | AM | — | — | 0.15~0.27 | 1.07 |
|    | 1000 | 15 | AM | 1.51~1.52 | 2.74 | | |
| 73 | 200 | 120 | AM | — | — | 0.18~0.30 | 1.15 |
|    | 1000 | 20 | AM | 1.50~1.51 | 2.88 | | |
| 74 | 200 | 111 | AM | — | — | 0.20~0.30 | 1.05 |
|    | 700 | 12 | AM | 1.51~1.52 | 2.55 | | |
| 75 | 200 | 123 | AM | — | — | 0.20~0.30 | 1.11 |
|    | 1000 | 31 | AM | 1.51~1.52 | 2.75 | | |
| 76 | 200 | 115 | AM | — | — | 0.30~0.40 | 1.06 |
|    | 1000 | 15 | AM + a + qu | 1.49~1.50 | 2.60 | | |
| 77 | 200 | 123 | AM | — | — | 0.15~0.30 | 1.15 |
|    | 1000 | 31 | AM | 1.48~1.49 | 2.54 | | |
| 78 | 200 | 108 | AM | — | — | 0.20~0.30 | 1.04 |
|    | 700 | 12 | AM | 1.43~1.44 | 2.51 | | |

COMPARATIVE EXAMPLE 1

A solution (A) was prepared by dissolving 200 g of the same tetraethyl silicate as used in Example 1 in 1.2 l of methanol, and a solution (B) was prepared by dissolving 54.0 g of the same tetrabutyl titanate as used in Example 4 in 1.2 l of methanol.

In the same reaction vessel as used in Example 1, the same ammoniac methanol solution as used in Example 1 was prepared.

The solutions (A) and (B) were simultaneously added to this ammoniac methanol solution with stirring from different dropping openings over a period of 2 hours at a reaction temperature of 20° C. Within several minutes from the point of initiation of the addition, the liquid reaction mixture became milky white. After completion of the addition, the liquid reaction mixture was stirred, and the solvent was removed from the liquid reaction mixture by an evaporator and the residue was dried under reduced pressure at 80° C. to obtain a milky white powder.

From the results of observation of a transmission type electron microscope photograph of the powder, it was confirmed that the particle size of the powder was in the range of from 0.01 to 0.03 μm and the powder was composed of an agglomerate of ultrafine particles having an indeterminate shape.

EXAMPLES 79 THROUGH 83

The procedures of Example 70 were repeated in the same manner except that mixed solutions shown in Table 11 were used. The obtained results are shown in Table 11. It was found that all of the obtained inorganic compounds were spherical.

TABLE 11

Composition of Mixed Solutions

| Example No. | Mixed Solution (A) Si(OC$_2$H$_5$)$_4$ (g) | Water (g) | Organic Metal Compound (g) | Mixed Solution (B) Si(OC$_2$H$_5$)$_4$ (g) | Organic Metal Compound (g) |
|---|---|---|---|---|---|
| 79 | 104 | 1.8 | Ti(OC$_4$H$_9$)$_4$ 17.0 | 104 | Sr(OCH$_3$)$_2$ = 5.0 NaOCH$_3$ = 1.0 |
| 80 | 104 | 1.8 | Ge(OC$_4$H$_9$)$_4$ 18.2 | 104 | Ca(OCH$_3$)$_2$ = 4.0 Al(O—sec-C$_4$H$_9$) = 1.0 |
| 81 | 104 | 1.8 | Ti(OC$_4$H$_9$)$_4$ 17.0 | 104 | NaOCH$_3$ = 2.0 Al(O—sec-C$_4$H$_9$) = 0.5 |
| 82 | 104 | 1.8 | Ti(OC$_4$H$_9$)$_4$ 17.0 | 104 | Al(O—sec-C$_4$H$_9$)$_3$ = 2.5 Sr(OCH$_3$) = 7.5 |
| 83 | 104 | 0 | Al(O—sec-C$_4$H$_9$)$_3$ 15.0 | 104 | NaOCH$_3$ = 1.0 Ca(OCH$_3$)$_2$ = 1.0 |

TABLE 11-continued

| Example No. | Calcining Temperature (°C.) | Specific Surface Area (m²/g) | X-Ray Analysis | Specific Gravity | Particle Size Range (μm) | Standard Deviation Value |
|---|---|---|---|---|---|---|
| 79 | 200 | 120 | AM | — | 0.16~0.24 | 1.04 |
|    | 800 | 21  | AM | 2.60 | | |
| 80 | 200 | 115 | AM | — | 0.11~0.23 | 1.11 |
|    | 700 | 20  | AM | 2.70 | | |
| 81 | 200 | 115 | AM | — | 0.18~0.27 | 1.10 |
|    | 700 | 12  | AM | 2.49 | | |
| 82 | 200 | 126 | AM | — | 0.10~0.23 | 1.11 |
|    | 700 | 40  | AM | 2.55 | | |
| 83 | 200 | 120 | AM | — | 0.10~0.30 | 1.30 |
|    | 700 | 45  | AM | 2.58 | | |

EXAMPLE 84

Preparation of Inorganic Compound

In 1.2 l of methanol were dissolved 4.0 g of 0.1% hydrochloric acid and 158 g of tetraethyl silicate [Si(OC$_2$H$_5$)$_4$, Ethyl Silicate 28 supplied by Nippon Colcoat Kagaku], and the solution was hydrolyzed at room temperature for about 2 hours with stirring. The hydrolyzed solution was added to a solution of 40.9 g of tetrabutyl titanate [Ti(O—n—C$_4$H$_9$)$_4$ supplied by Nippon Soda] in 0.5 l of isopropanol with stirring to form a mixed solution of hydrolyzed tetraethyl silicate and tetrabutyl titanate.

A glass vessel equipped with a stirrer and having an inner capacity of 10 l was charged with 2.5 l of methanol, and 500 g of aqueous ammonia (having a concentration of 25% by weight) was added thereto to form an ammoniac methanol solution. Then, a solution of 4.0 g of tetraethyl silicate in 100 ml of methanol as the organic silicon compound solution for formation of silica seeds was added to the ammoniac methanol solution with stirring over a period of about 5 minutes, and when the liquid reaction mixture became slightly milky white within 5 minutes from the point of completion of the addition, the above-mentioned mixed solution was added to the liquid reaction mixture with stirring at 20° C. over a period of about 2 hours to precipitate a reaction product. Then, a solution of 128 g of tetraethyl silicate in 0.5 l of methanol was added to the liquid reaction mixture containing the precipitated reaction product with stirring over a period of about 2 hours. The liquid reaction mixture was stirred for 1 hour after completion of the addition, and the solvent was removed from the milky white liquid reaction mixture by an evaporator. The residue was dried under reduced pressure at 80° C. to obtain a milky white powder.

The milky white powder was calcined at 900° C. for 4 hours and dispersed in a grinding machine to obtain an inorganic compound comprising silica and titania as main constituents. When a scanning type electron microscope photograph of this inorganic compound was examined, it was found that the particle size was in the range of from 0.10 to 0.20 μm, the average particle size was 0.13 μm, the particles had a shape of a true sphere and the standard deviation value of the particle size was 1.08, and it also was found that the specific surface area was 20 m²/g. The obtained inorganic compound was surface-treated with γ-methacryloxypropyltrimethoxysilane according to the following method.

γ-Methacryloxypropyltrimethoxydilane was added to the inorganic compound in an amount of 8% by weight, and the mixture was refluxed at 80° C. in a water-methanol solvent for 2 hours and the solvent was removed by an evaporator. The residue was dried in vacuo.

Preparation of Composite Resin

A paste was obtained by mixing 10 g of the surface-treated inorganic compound, 3.6 g of a vinyl monomer mixture comprising 60% by weight of Bis-GMA and 40% by weight of TEGDMA, 2.0% by weight, based on the vinyl monomer mixture, of benzoyl peroxide as the organic peroxide and 0.1% by weight, based on the vinyl monomer mixture, of 2,5-di-tert-butyl-4-methylphenol. This paste was designated as "paste (B)".

A paste was obtained by mixing 10 g of the above-mentioned inorganic compound, 3.6 of the above-mentioned vinyl monomer mixture, 1.2% by weight, based on the vinyl monomer mixture, of N,N-bis-(2-hydroxyethyl)-4-methylaniline as the tertiary amine and 0.02% by weight, based on the vinyl monomer mixture, of 2,5-di-tert-butyl-4-methylphenol. This paste was designated as "paste (A)".

Equal amounts of the pastes (A) and (B) were mixed and kneaded at room temperature for 30 seconds.

The properties of the obtained composite resin were determined. It was found that the compressive strength was 3,800 Kg/cm², the flexural strength was 810 Kg/cm², the surface roughness was 0.4 μm and the wear depth by a toothbrush was 4.0 μm.

EXAMPLES 85 THROUGH 89

Pastes (A) and (B) were prepared in the same manner as described in Example 84 except that a vinyl monomer mixture shown in Table 12 was used and N,N-dimethyl-p-toluidine was used as the tertiary amine. Equal amounts of both the pastes were mixed and kneaded at room temperature for 30 seconds to effect polymerization. The properties of the obtained composite resin were determined to obtain results shown in Table 12.

TABLE 12

| Example No. | Composition of Vinyl Monomer Mixture[1] | Amount (% by weight) of Inorganic Compound Filled in Composite Resin | Properties of Composite Resin | | | | |
|---|---|---|---|---|---|---|---|
| | | | Compressive Strength (Kg/cm²) | Flexural Strength (Kg/cm²) | Wear Depth by Tooth brush (μm) | Surface Roughness (μm) | Surface Hardness |
| 85 | Bis-GMA (70) TEGDMA (30) | 73.5 | 3,670 | 800 | 4.5 | 0.4 | 65 |

TABLE 12-continued

| Example No. | Composition of Vinyl Monomer Mixture[1] | Amount (% by weight) of Inorganic Compound Filled in Composite Resin | Properties of Composite Resin | | | | |
|---|---|---|---|---|---|---|---|
| | | | Compressive Strength (Kg/cm$^2$) | Flexural Strength (Kg/cm$^2$) | Wear Depth by Tooth brush ($\mu$m) | Surface Roughness ($\mu$m) | Surface Hardness |
| 86 | Bis-GMA (42) TEGDMA (18) TMPT (30) | 73.5 | 4,100 | 880 | 4.0 | 0.4 | 67 |
| 87 | TMM-3M (50) TMM-4M (50) | 72.0 | 4,200 | 950 | 4.0 | 0.4 | 68 |
| 88 | Bis-GMA (42) TEGDMA (18) TMM-3M (15) TMM-4M (15) | 71.0 | 3,820 | 900 | 3.5 | 0.3 | 67 |
| 89 | Bis-GMA (50) U-4HMA (40) MMA (10) | 72.5 | 4,040 | 960 | 4.1 | 0.4 | 67 |

Note
[1]Each parenthesized value indicates the amount (% by weight).

EXAMPLES 90 THROUGH 94

Preparation of Inorganic Compound

In 0.2 l of methanol were dissolved 1.8 g of 0.5% hydrochloric acid and 104 g of tetraethyl silicate [Si-(OC$_2$H$_5$)$_4$, Ethyl Silicate 28 supplied by Nippon Colcoat Kagaku], and hydrolysis was carried out by stirring this solution for about 1 hour at room temperature. A solution of 17.0 g of tetrabutyl titanate [Ti(O—n—C$_4$H$_9$)$_4$ supplied by Nippon Soda] in 1.0 l of isopropanol was added to the hydrolyzed solution with stirring to form a mixed solution (A) of hydrolyzed tetraethyl silicate and tetrabutyl titanate. Then, 7.8 g of barium bis-isopentoxide, 104 g of tetraphenyl silicate and 0.2 g of aluminum tri-sec-butoxide were dissolved in 1.0 l of methanol, and the solution was refluxed at 90° C. in a nitrogen atmosphere for 30 minutes and the temperature was returned to room temperature to form a mixed solution (B). The mixed solution (A) was mixed with the mixed solution (B) at room temperature to form a mixed solution (C).

A glass reaction vessel equipped with a stirrer and having an inner capacity of 10 l was charged with 2.5 l of methanol, and 500 g of aqueous ammonia (having a concentration of 25% by weight) was added to form an ammoniac alcohol solution. The above-mentioned mixed solution (C) was added to the so-formed solution with stirring over a period of about 4 hours while maintaining the liquid temperature at 20° C. Within several minutes from the point of initiation of the addition, the liquid reaction became milky white. After completion of the addition, the liquid reaction mixture was further stirred for 1 hour. The solvent was removed from the milky white liquid reaction mixture by an evaporator and the residue was dried under reduced pressure at 80° C. to form a milky white powder.

The milky white powder was calcined at 700° C. for 4 hours and dispersed in grinding machine to obtain an inorganic compound comprising silica, titania and barium oxide as main constituents. When a scanning electron microscope photograph of this inorganic compound was examined, it was found that the powder had a spherical shape and a particle size of 0.12 to 0.26 $\mu$m and that the standard deviation value of the particle size was 1.06. The specific surface area as determined according to the BET method was 30 m$^2$/g.

In the X-ray analysis, a gentle mountain-like absorption with the point of 2$\theta$=25° being as the center was observed, and it was confirmed that the powder had an amorphous structure.

The obtained inorganic compound was surface-treated with $\gamma$-methacryloxypropyltrimethoxysilane according to the following method described in Example 84.

Preparation of Composite Resin

Pastes (A) and (B) were prepared in the same manner as described in Example 84 except that this surface-treated inorganic compound and a vinyl monomer mixture shown in Table 13 were used and lauroyl peroxide (2.5% by weight) was used as the organic peroxide. Equal amounts of both the pastes were mixed and kneaded at room temperature for 1 minute to effect polymerization. The properties of the obtained composite resin were determined to obtain results shown in Table 13.

TABLE 13

| Example No. | Composition of[1] Vinyl Monomer Mixture | Amount (% by weight of Inorganic Compound Filled in Composite Resin | Properties of Composite Resin | | | | |
|---|---|---|---|---|---|---|---|
| | | | Compressive Strength (Kg/cm$^2$) | Flexural Strength (Kg/cm$^2$) | Wear Depth by Toothbrush ($\mu$m) | Surface Roughness ($\mu$m) | Surface Hardness |
| 90 | Bis-GMA (60) TEGDMA (40) | 70.5 | 3,570 | 1,010 | 5.0 | 0.4 | 63 |
| 91 | Bis-GMA (54) DEGDMA (36) TMPT (10) | 69.5 | 3,710 | 820 | 4.0 | 0.4 | 65 |
| 92 | TMM-3M (30) TMM-4M (70) | 69.0 | 4,010 | 910 | 4.5 | 0.4 | 64 |
| 93 | Bis-GMA (42) TEGDMA (18) TMPT (15) TMM-4M (15) | 70.4 | 3,830 | 970 | 4.0 | 0.5 | 64 |
| 94 | Bis-MPP (50) U-4HMA (40) | 72.1 | 3,920 | 830 | 4.0 | 0.3 | 65 |

TABLE 13-continued

|  | | Properties of Composite Resin | | | | |
|---|---|---|---|---|---|---|
| Example No. | Composition of[1] Vinyl Monomer Mixture | Amount (% by weight of Inorganic Compound Filled in Composite Resin | Compressive Strength (Kg/cm$^2$) | Flexural Strength (Kg/cm$^2$) | Wear Depth by Toothbrush ($\mu$m) | Surface Rough- ness ($\mu$m) | Surface Hardness |
|  | MMA (10) | | | | | | |

Note
[1]Each parenthesized value indicates the amount (% by weight).

EXAMPLES 95 THROUGH 99

Preparation of Inorganic Compound

In 0.2 l of isopropyl alcohol were dissolved 52 g of the same tetraethyl silicate as used in Example 1 and 15.6 g of zirconium tetrabutoxide [Zr(OC$_4$H$_9$)$_4$], and the solution was refluxed at 100° C. for 30 minutes in a nitrogen atmosphere. The temperature was returned to room temperature to form a mixed solution (A). Then, 52 g of tetraethyl silicate and 6.1 g of strontium bis-methoxide were dissolved in 0.2 l of methanol, and the solution was refluxed at 80° C. for 30 minutes in a nitrogen atmosphere and the temperature was returned to room temperature to form a mixed solution (B). The mixed solution (A) was mixed with the mixed solution (B) to form a mixed solution (C).

A glass reaction vessel equipped with a stirrer and having an inner capacity of 10 l was charged with 2.4 l of methanol, and 500 g of aqueous ammonia (having a concentration of 25% by weight) was added to form an ammoniac alcohol solution. The above-mentioned mixed solution (C) was added to the so-formed solution with stirring over a period of about 4 hours while maintaining the liquid temperature at 20° C. Then, a solution of 50 g of tetraethyl silicate in 0.5 l of methanol was added to the liquid reaction mixture containing the precipitated reaction product over a period of about 2 hours. The liquid reaction mixture was stirred for 1 hour after completion of the addition, and the solvent was removed from the milky white liquid reaction mixture by an evaporator. The residue was dried under reduced pressure to obtain a milky white powder.

The milky white powder was calcined at 900° C. for 3 hours and dispersed in a grinding machine to obtain an inorganic compound comprising silica zirconia and strontium oxide as main constituents.

When the powder was observed by scanning type electron microscope photography, it was found that the powder had a spherical shape and a particle size of 0.10 to 0.25 $\mu$m, and the average particle size was 0.17 $\mu$m and that the standard deviation value of the particle size was 1.25. The specific surface area as determined according to the BET method was 26 m$^2$/g.

The obtained inorganic compound was surface-treated with $\gamma$-methacryloxypropyltrimethoxysilane according to the following method described in Example 84.

Preparation of Composite Resin

Pastes (A) and (B) were prepared in the same manner as described in Example 84 except that a vinyl monomer mixture shown in Table 14 was used and benzoyl peroxide as the organic peroxide (1.5% by weight) and hydroquinone monomethyl ether as the polymerization inhibitor were used. Equal amounts of both the pastes were mixed and kneaded at room temperature for 30 seconds to effect polymerization. The properties of the obtained composite resin were determined to obtain results shown in Table 14.

TABLE 14

|  | | | Properties of Composite Resin | | | | |
|---|---|---|---|---|---|---|---|
| Example No. | Composition of[1] Vinyl Monomer Mixture | Amount (% by weight of Inorganic Compound Filled in Composite Resin | Compressive Strength (Kg/cm$^2$) | Flexural Strength (Kg/cm$^2$) | Wear Depth by Toothbrush ($\mu$m) | Surface Rough- ness ($\mu$m) | Surface Hardness |
| 95 | Bis-GMA (80) DEGDMA (20) | 68.5 | 3,520 | 830 | 5.5 | 0.5 | 60 |
| 96 | Bis-MPP (60) TEGDMA (10) TMPT (30) | 71.0 | 3,730 | 815 | 4.5 | 0.4 | 62 |
| 97 | TMM-3M (40) TMM-4M (60) | 70.0 | 4,010 | 830 | 6.0 | 0.5 | 61 |
| 98 | Bis-GMA (50) TEGDMA (20) TMM-3M (10) TMM-4M (20) | 69.3 | 3,870 | 910 | 5.5 | 0.4 | 60 |
| 99 | Bis-GMA (60) TEGDMA (30) TMPT (10) | 70.0 | 3,650 | 880 | 4.5 | 0.4 | 62 |

Note
[1]Each parenthesized value indicates the amount (% by weight).

EXAMPLES 100 THROUGH 104

Preparation of Inorganic Compound

In 1.2 l of methanol were dissolved 4.0 g of 0.1% hydrochloric acid and 158 g of the same tetraethyl silicate as used in Example 1, and the solution was hydrolyzed at room temperature for about 1 hour with stirring. The hydrolyzed solution was added to a solution of 40 g of tetrabutyl titanate in 0.5 l of isopropanol with stirring to form a mixed solution (A) of hydrolyzed tetraethyl silicate and tetrabutyl titanate. Then, 0.2 g of sodium methylate was dissolved in 0.5 l of methanol to form a mixed solution (B). The mixed solution (A) was mixed with the mixed solution (B) at room temperature to form a mixed solution (C).

A glass reaction vessel equipped with a stirrer and having an inner capacity of 10 l was charged with 2.5 l of methanol, and 500 g of aqueous ammonia (having a concentration of 25% by weight) was added to form an ammoniac alcohol solution. A solution of 5.0 g of tetraethyl silicate in 100 ml of methanol was added over a period of 10 minutes to the ammoniac alcohol solution, and the above-mentioned mixed solution (C) was added to the so-formed solution with stirring over a period of about 6 hours while maintaining the liquid temperature at 20° C. to precipitate a reaction product. Then, a solution of 128 g of tetraethyl silicate and 0.1 g of sodium methylate in 0.5 l of methanol was added to the liquid reaction mixture containing the precipitated reaction product over a period of about 3 hours. The liquid reaction mixture was stirred for 1 hour after completion of the addition, and the solvent was removed from the milky white liquid reaction mixture by an evaporator. The residue was dried under reduced pressure at 100° C. to obtain a milky white powder.

The milky white powder was calcined at 1000° C. for 1 hour and dispersed in a grinding machine to obtain an inorganic compound comprising silica, titania and sodium oxide as main constituents. When a scanning type electron microscope photograph of this inorganic compound was examined, it was found that the particle size was in the range of from 0.20 to 0.40 μm, the average particle size was 0.28 μm, the particles had a spherical shape and the standard deviation value of the particle size was 1.25, and it also was found that the specific surface area was 15 m²/g. The obtained inorganic compound was surface-treated with γ-methacryloxypropyltrimethoxysilane according to the following method described in Example 84.

Pastes (A) and (B) were prepared in the same manner as described in Example 84 except that a vinyl monomer mixture shown in Table 15 was used and N,N-dimethyl-p-toluidine (1.5% by weight) was used as the tertiary amine. Equal amounts of both the pastes were mixed and kneaded at room temperature for 30 seconds to effect polymerization. The properties of the obtained composite resin were determined to obtain results shown in Table 15.

mixture was sufficiently kneaded to obtain a paste. The paste was allowed to stand in vacuum to remove air bubbles and ethanol. The amount of the inorganic compound filled in the paste from which air bubbles and ethanol had been removed was 78.0% by weight. Then, the paste was polymerized under a nitrogen pressure of 5 Kg/cm² at a polymerization temperature of 120° C. for a polymerization time of 1 hour to obtain a polymer. The polymer was pulverized in a mortar to a size smaller than 6 mm. The pulverized polymer was crushed in a crusher for 1 hour to obtain a composite resin filler capable of passing through a 250-mesh sieve.

The specific gravity of the composite resin filler was 2.21 and the surface hardness was 72.

Preparation of Composite Resin

Then, 10 g of a filler mixture comprising 50% by weight of the above-mentioned composite resin filler and 50% by weight of the inorganic compound used in Example 84 was mixed with 3.2 g of a vinyl monomer mixture comprising 60% by weight of Bis-GMA and 40% by weight of TEGDMA and 2.0% by weight, based on the vinyl monomer mixture, of benzoyl peroxide and 0.1% by weight, based on the vinyl monomer mixture, of 2,5-di-tert-butyl-4-methylphenol to obtain a paste (B).

A paste (A) was prepared by mixing 10 g of the above-mentioned filler mixture with 3.2 g of the above-mentioned vinyl monomer mixture, 1.2% by weight, based on the vinyl monomer mixture, of N,N-bis-(2-hydroxyethyl)-4-methylaniline and 0.02% by weight, based on the vinyl monomer mixture, of 2,5-di-tert-butyl-4-methylphenol.

Equal amounts of the pastes (A) and (B) were mixed and kneaded at room temperature for 30 seconds to effect polymerization. The properties of the composite resin were determined. The compressive strength was 3710 Kg/cm², the flexural strength was 890 Kg/cm², the surface roughness was 0.5 μm, the surface hardness was 62 and the wear depth by a toothbrush was 5.5 μm.

TABLE 15

| | | | Properties of Composite Resin | | | | |
|---|---|---|---|---|---|---|---|
| Example No. | Composition of[1] Vinyl Monomer Mixture | Amount (% by weight of Inorganic Compound Filled in Composite Resin | Compressive Strength (Kg/cm²) | Flexural Strength (Kg/cm²) | Wear Depth by Toothbrush (μm) | Surface Roughness (μm) | Surface Hardness |
| 100 | Bis-GMA (80) NPG (20) | 74.0 | 3,550 | 810 | 5.5 | 0.6 | 64 |
| 101 | Bis-GMA (50) TEGDMA (40) TMPT (10) | 74.0 | 3,860 | 850 | 6.0 | 0.7 | 63 |
| 102 | TMPT (70) TMM-4M (30) | 74.5 | 4,080 | 940 | 6.0 | 0.4 | 63 |
| 103 | Bis-GMA (40) TEGDMA (20) TMM-3M (20) TMM-4M (20) | 74.5 | 3,960 | 890 | 4.5 | 0.4 | 62 |
| 104 | Bis-GMA (40) U-4TMA (40) TEGDMA (20) | 75.0 | 3,950 | 960 | 5.0 | 0.5 | 64 |

EXAMPLE 105

Preparation of Composite Resin Filler

The surface-treated inorganic compound obtained in Example 84 was mixed with a vinyl monomer mixture comprising 60% by weight of Bis-GMA and 40% by weight of TEGDMA, azobisisobutyronitrile (0.5 part by weight per 100 parts by weight of the vinyl monomer mixture) and ethanol (15 parts by weight per 100 parts by weight of the vinyl monomer mixture) and the

EXAMPLES 106 THROUGH 110

Pastes (A) and (B) were prepared in the same manner as described in Example 105 except that a filler mixture and a vinyl monomer mixture shown in Table 16 were used. Equal amounts of both the pastes were mixed and kneaded at room temperature for 30 seconds to effect polymerization. The properties of the obtained composite resin were determined to obtain results shown in Table 16.

TABLE 16

| Example No. | Amount (% by weight) of Filler Mixture in Composite Resin | Kind of Vinyl Monomer Mixture | Composition of Filler Mixture (% by weight) | |
|---|---|---|---|---|
| | | | Inorganic Compound of Example 84 | Composite Resin Filler of Example 106 |
| 106 | 75.0 | Mixture of Example 85 | 0 | 100 |
| 107 | 84.5 | Mixture of Example 86 | 30 | 70 |
| 108 | 77.8 | Mixture of Example 87 | 50 | 50 |
| 109 | 77.0 | Mixture of Example 88 | 60 | 40 |
| 110 | 75.0 | Mixture of Example 89 | 80 | 20 |

| Example No. | Properties of Composite Resin | | | | |
|---|---|---|---|---|---|
| | Compressive Strength (Kg/cm$^2$) | Flexural Strength (Kg/cm$^2$) | Wear Depth by Toothbrush ($\mu$m) | Surface Roughness ($\mu$m) | Surface Hardness |
| 106 | 3,100 | 810 | 7.0 | 0.6 | 60 |
| 107 | 3,310 | 900 | 5.5 | 0.5 | 61 |
| 108 | 3,900 | 1,010 | 4.5 | 0.5 | 63 |
| 109 | 3,820 | 890 | 5.0 | 0.5 | 63 |
| 110 | 4,050 | 750 | 4.0 | 0.4 | 63 |

EXAMPLES 111 THROUGH 115 ite resin were determined to obtain results shown in Table 17.

TABLE 17

| Example No. | Amount (% by weight) of Filler Mixture in Composite Resin | Kind of Vinyl Monomer Mixture | Composition of Filler Mixture (% by weight) | |
|---|---|---|---|---|
| | | | Inorganic Compound of Example 90 | Composite Resin Filler of Example 111 |
| 111 | 74.5 | Mixture of Example 90 | 0 | 100 |
| 112 | 83.0 | Mixture of Example 91 | 30 | 70 |
| 113 | 75.8 | Mixture of Example 92 | 50 | 50 |
| 114 | 75.0 | Mixture of Example 93 | 60 | 40 |
| 115 | 73.0 | Mixture of Example 94 | 80 | 20 |

| Example No. | Properties of Composite Resin | | | | |
|---|---|---|---|---|---|
| | Compressive Strength (Kg/cm$^2$) | Flexural Strength (Kg/cm$^2$) | Wear Depth by Toothbrush ($\mu$m) | Surface Roughness ($\mu$m) | Surface Hardness |
| 111 | 3,040 | 890 | 6.0 | 0.5 | 60 |
| 112 | 3,820 | 750 | 7.0 | 0.6 | 60 |
| 113 | 3,800 | 840 | 5.5 | 0.5 | 62 |
| 114 | 3,700 | 850 | 5.0 | 0.4 | 62 |
| 115 | 3,800 | 840 | 5.0 | 0.5 | 63 |

Preparation of Composite Resin Filler

The surface-treated inorganic compound obtained in Example 103 was mixed with the vinyl monomer mixture of Example 87, lauroyl peroxide (0.2 part by weight per 100 parts by weight of the vinyl monomer mixture) and ethanol (10 parts by weight per 100 parts by weight of the vinyl monomer mixture) and the mixture was sufficiently kneaded to obtain a paste. The paste was allowed to stand in vacuum to remove air bubbles and ethanol. The amount of the inorganic compound filled in the paste from which air bubbles and ethanol had been removed was 76% by weight. Then, the paste was polymerized under an argon pressure of 3 Kg/cm$^2$ at a polymerization temperature of 90° C. for a polymerization time of 1 hour to obtain a polymer. The polymer was pulverized in a ball mill for 5 hours. The pulverized polymer was crushed in a crusher for 1 hour to obtain a composite resin filler capable of passing through a 400-mesh sieve.

The specific gravity of the composite resin filler was 2.40 and the surface hardness was 65.

Preparation of Composite Resin

Pastes (A) and (B) were prepared in the same manner as described in Example 105 except that a filler mixture and a vinyl monomer mixture shown in Table 17 were used. Equal amounts of both the pastes were mixed and kneaded at room temperature for 30 seconds to effect polymerization. The properties of the obtained composite resin were determined to obtain results shown in Table 17.

EXAMPLES 116 THROUGH 120

Preparation of Composite Resin Filler

The surface-treated inorganic compound obtained in Example 86 was mixed with the vinyl monomer mixture of Example 80, methylethyl ketone peroxide (1.0 part by weight per 100 parts by weight of the vinyl monomer mixture) and ethanol (20 parts by weight per 100 parts by weight of the vinyl monomer mixture) and the mixture was sufficiently kneaded to obtain a paste. The paste was allowed to stand in vacuum to remove air bubbles and ethanol. The amount of the inorganic compound filled in the paste from which air bubbles and ethanol had been removed was 80% by weight. Then, the paste was polymerized under a nitrogen pressure of 2 Kg/cm$^2$ at a polymerization temperature of 120° C. for a polymerization time of 4 hours to obtain a polymer. The polymer was pulverized in a ball mill for 6 hours. The pulverized polymer was crushed in a crusher for 1 hour to obtain a composite resin filler capable of passing through a 200-mesh sieve.

The specific gravity of the composite resin filler was 2.51 and the surface hardness was 75.

Preparation of Composite Resin

Pastes (A) and (B) were prepared in the same manner as described in Example 90 except that a filler mixture and a vinyl monomer mixture shown in Table 18 were used. Equal amounts of both the pastes were mixed and kneaded at room temperature for 30 seconds to effect polymerization. The properties of the obtained composite resin were determined to obtain results shown in Table 18.

The specific gravity of the composite resin filler was 2.01 and the surface hardness was 70.

Pastes (A) and (B) were prepared in the same manner as described in Example 100 except that a filler mixture and a vinyl monomer mixture shown in Table 19 were used. Equal amounts of both the pastes were mixed and kneaded at room temperature for 1 minute to effect polymerization. The properties of the obtained composite resin were determined to obtain results shown in Table 19.

TABLE 18

| Example No. | Amount (% by weight) of Filler Mixture in Composite Resin | Kind of Vinyl Monomer Mixture | Composition of Filler Mixture (% by weight) | |
|---|---|---|---|---|
| | | | Inorganic Compound of Example 95 | Composite Resin Filler of Example 116 |
| 116 | 73.0 | mixture of Example 95 | 0 | 100 |
| 117 | 80.5 | mixture of Example 96 | 30 | 70 |
| 118 | 75.5 | mixture of Example 97 | 50 | 50 |
| 119 | 75.0 | mixture of Example 98 | 60 | 40 |
| 120 | 72.0 | mixture of Example 99 | 80 | 20 |

| Example No. | Properties of Composite Resin | | | | |
|---|---|---|---|---|---|
| | Compressive Strength (Kg/cm$^2$) | Flexural Strength (Kg/cm$^2$) | Wear Depth by Toothbrush ($\mu$m) | Surface Roughness ($\mu$m) | Surface Hardness |
| 116 | 3,000 | 910 | 5.5 | 0.7 | 59 |
| 117 | 3,520 | 880 | 4.5 | 0.7 | 60 |
| 118 | 3,700 | 750 | 5.0 | 0.6 | 62 |
| 119 | 3,520 | 900 | 5.0 | 0.4 | 62 |
| 120 | 3,550 | 880 | 8.0 | 0.9 | 64 |

TABLE 19

| Example No. | Amount (% by weight) of Filler Mixture in Composite Resin | Kind of Vinyl Monomer Mixture | Composition of Filler Mixture (% by weight) | |
|---|---|---|---|---|
| | | | Inorganic Compound of Example 100 | Composite Resin Filler of Example 121 |
| 121 | 76.5 | mixture of Example 100 | 0 | 100 |
| 122 | 85.0 | mixture of Example 101 | 30 | 70 |
| 123 | 78.2 | mixture of Example 102 | 50 | 50 |
| 124 | 77.5 | mixture of Example 103 | 60 | 40 |
| 125 | 75.5 | mixture of Example 104 | 80 | 20 |

| Example No. | Properties of Composite Resin | | | | |
|---|---|---|---|---|---|
| | Compressive Strength (Kg/cm$^2$) | Flexural Strength (Kg/cm$^2$) | Wear Depth by Toothbrush ($\mu$m) | Surface Roughness ($\mu$m) | Surface Hardness |
| 121 | 2,900 | 940 | 8.0 | 0.6 | 60 |
| 122 | 3,550 | 900 | 7.0 | 0.5 | 60 |
| 123 | 3,800 | 880 | 6.0 | 0.4 | 62 |
| 124 | 3,500 | 890 | 5.0 | 0.5 | 62 |
| 125 | 3,800 | 750 | 5.0 | 0.6 | 62 |

EXAMPLES 121 THROUGH 125

Preparation of Composite Resin Filler

The surface-treated inorganic compound obtained in Example 102 was mixed with the vinyl monomer mixture of Example 85 and benzoyl peroxide (0.1 part by weight per of the vinyl monomer mixture), per 100 parts by and the mixture was sufficiently kneaded to obtain a paste. The paste was allowed to stand in vacuum to remove air bubbles. The amount of the inorganic compound filled in the paste from which air bubbles had been removed was 65.0% by weight. Then, the paste was polymerized under a nitrogen pressure of 5 Kg/cm$^2$ at a polymerization temperature of 90° C. for a polymerization time of 4 hours to obtain a polymer. The polymer was pulverized in a vibrating ball mill for 1 hour. The pulverized polymer was crushed in a crusher for 1 hour to obtain a composite resin filler capable of passing through a 250-mesh sieve.

What is claimed is:

1. Spherical particles comprising an amorphous composition composed of (1) silica, (2) an oxide of a metal from Group IV of the Periodic Table and (3) at least one oxide of a metal selected from the group consisting of metals of Group I, Group II and Group III of the Periodic Table, and containing 0.01 to 20 mole %, based on silica (1), of said components (2) and (3), said components (1), (2) and (3) being present in the chemically bonded state and being inseparable from one another, said particles having a particle size of 0.1 to 1.0 $\mu$m and a narrow particle size distribution having a standard deviation value smaller than 1.30.

2. The spherical particles of claim 1 wherein the component (3) comprises at least one oxide of a metal of Group I of the Periodic Table.

3. The spherical particles of claim 2 wherein the Group I metal is sodium, lithium or potassium or mixtures thereof.

4. The spherical particles of claim 1 wherein the component (3) comprises at least one oxide of a metal of Group II of the Periodic Table.

5. The spherical particles of claim 4 wherein the Group II metal is magnesium, calcium, strontium, barium or mixtures thereof.

6. The spherical particles of claim 1 wherein component (3) comprises at least one oxide of a metal of Group III of the Periodic Table.

7. The spherical particles of claim 6 wherein the Group III metal is aluminum, boron, gallium, scandium, lanthanum, yttrium, indium or mixtures thereof.

8. The spherical particles of claim 1 which comprise seeds composed of silicon dioxide as a core and said amorphous composition surrounding said core.

9. The spherical particles of claim 1 which comprise silica seed as a central core, a layer on the central core comprised of said amorphous composition, and a surface layer covering said amorphous composition layer and composed mainly of silica.

10. The spherical particles of claim 9 having hydroxyl groups bonded to the surface thereof in an amount of about 1.0 to 2.0 millimoles per gram.

11. The spherical particles of claim 1, which have a specific surface area of 1 to 100 m$^2$/g.

12. The spherical particles of claim 11 having hydroxyl groups bonded to the surface thereof in an amount of about 0.01 to 0.10 millimole per gram.

13. The spherical particles of claim 1, wherein the oxide of the metal of Group IV is titanium oxide, zirconium oxide, germanium oxide or tin oxide.

14. The spherical particles of claim 1, wherein the components (2) and (3) are present in an amount of 0.01 to 15 mole% based on silica in total.

15. The spherical particles of claim 1, wherein the particles have a refractive index of from 1.35 to 1.70.

16. A process for the preparation of an amorphous inorganic composition, which comprises partially hydrolyzing a hydrolyzable organic silicon compound, in an organic solvent, mixing (1) the partially hydrolyzed organic silicon compound, (2) a hydrolyzable organic compound of a metal of Group IV of the Periodic Table, and (3) a hydrolyzable organic compound of at least one metal (M) selected from the group consisting of metals of the Groups I, II and III of the Periodic Table, the proportion of (2) and (3) being in the range of 0.01 to 20 mole % based on SiO$_2$, to an alkaline solvent capable of dissolving said organic silicon compound and said organic metal compounds therein but substantially incapable of dissolving a reaction product of both the organic silicon compound and the organic metal compounds therein, and effecting the hydrolysis to precipitate the reaction product.

17. A process according to claim 16, wherein the precipitated reaction product is sintered.

18. A process according to claim 16, wherein the hydrolyzable organic silicon compound is a partial hydrolysis product of a hydrolyzable organic silicon compound.

19. A process for the preparation of an amorphous inorganic composition which comprises partially hydrolyzing a hydrolyzable organic silicon compound, in an organic solvent, mixing (1) the partially hydrolyzed organic silicon compound, (2) a hydrolyzable organic compound of a metal of Group IV of the Periodic Table, and (3) a hydrolyzable organic compound of at least one metal selected from the group consisting of metals of the Groups I, II and III of the Periodic Table, the proportion of (2) and (3) being in the range of 0.01 to 20 mole %, based on SiO$_2$, to an alkaline solvent capable of dissolving said organic silicon compound and said organic metal compounds therein but substantially incapable of dissolving a reaction product of both the organic silicon compound and the organic metal compounds therein, effecting the hydrolysis to precipitate the reaction product, adding a hydrolyzable organic silicon compound to the reaction mixture, and effecting the hydrolysis.

20. A process according to claim 19, wherein the reaction product obtained following hydrolysis with the hydrolyzable organic silicon compound is sintered.

21. A process according to claim 19 wherein the hydrolyzable organic silicon compound is a partial hydrolysis product of the hydrolyzable organic silicon compound.

* * * * *

UNITED STATES PATENT AND TRADEMARK OFFICE
CERTIFICATE OF CORRECTION

PATENT NO. : 4,764,497
DATED : August 16, 1988
INVENTOR(S) : SHIGEKI YUASA, ET AL.

It is certified that error appears in the above-identified patent and that said Letters Patent is hereby corrected as shown below:

IN THE CLAIMS

Please add the following claim which was omitted:

--22. The spherical particles of claim 1 which have a specific surface area of 100 to 200 $m^2/g$.--

Claim 10, line 1, delete "9", insert --22--.

Signed and Sealed this

Sixth Day of June, 1989

Attest:

DONALD J. QUIGG

Attesting Officer

Commissioner of Patents and Trademarks